(12) United States Patent
Schmitz

(10) Patent No.: US 12,156,796 B2
(45) Date of Patent: Dec. 3, 2024

(54) HYGIENE ARTICLE COMPRISING A SKIN PROTECTION SHEET WITH WELL POSITIONED OPENING(S)

(71) Applicant: Concepts for Success (C4S), Euskirchen (DE)

(72) Inventor: Christoph Schmitz, Euskirchen (DE)

(73) Assignee: Concepts for Success (C4S), Euskirchen (DE)

( * ) Notice: Subject to any disclaimer, the term of this patent is extended or adjusted under 35 U.S.C. 154(b) by 729 days.

(21) Appl. No.: 17/273,827

(22) PCT Filed: Sep. 5, 2019

(86) PCT No.: PCT/EP2019/073716
§ 371 (c)(1),
(2) Date: Mar. 5, 2021

(87) PCT Pub. No.: WO2020/049109
PCT Pub. Date: Mar. 12, 2020

(65) Prior Publication Data
US 2021/0315745 A1     Oct. 14, 2021

(30) Foreign Application Priority Data

Sep. 6, 2018 (GB) ..................................... 1814501
Dec. 21, 2018 (GB) ..................................... 1821151
(Continued)

(51) Int. Cl.
*A61F 13/513* (2006.01)
*A61F 13/15* (2006.01)
(Continued)

(52) U.S. Cl.
CPC ...... *A61F 13/513* (2013.01); *A61F 13/15747* (2013.01); *A61F 13/49* (2013.01);
(Continued)

(58) Field of Classification Search
CPC .......... A61F 13/15747; A61F 13/47272; A61F 13/49; A61F 13/49473; A61F 13/495;
(Continued)

(56) References Cited

U.S. PATENT DOCUMENTS

2002/0111598 A1*  8/2002  Vogt ....................... A61F 13/495
                                                   604/385.19
2004/0039363 A1*  2/2004  Sugiyama ............. A61F 13/511
                                                   604/385.24
(Continued)

FOREIGN PATENT DOCUMENTS

GB     2497545 A    6/2013
GB     2519291 A    4/2015

OTHER PUBLICATIONS

International Search Report and Written Opinion for International Patent Application No. PCT/EP209/073716 mailed Nov. 22, 2019, 12 pages.

*Primary Examiner* — Leslie A Lopez
*Assistant Examiner* — Jihad Dakkak
(74) *Attorney, Agent, or Firm* — Jordan IP Law, LLC

(57) ABSTRACT

The present invention relates to the field of hygiene appliances, in particular to a means for reducing soiling of the skin of a wearer upon defecation. In particular, it relates to a hygiene article comprising a skin protection sheet that comprises a discontinuity as a faeces passageway, such as an opening or a slit. In use, the sheet and the discontinuity are urged towards the anus by a pull means and spread open by a spreading means, such that faeces can pass through the discontinuity but are separated from the skin of the wearer elsewhere.

9 Claims, 16 Drawing Sheets

(30) Foreign Application Priority Data

Apr. 17, 2019 (GB) .................................... 1905408
Aug. 1, 2019 (GB) .................................... 1911011

(51) Int. Cl.
*A61F 13/49* (2006.01)
*A61F 13/514* (2006.01)
*A61F 13/53* (2006.01)

(52) U.S. Cl.
CPC ............ *A61F 13/514* (2013.01); *A61F 13/53* (2013.01); *A61F 2013/15869* (2013.01); *A61F 2013/49074* (2013.01); *A61F 2013/51338* (2013.01)

(58) Field of Classification Search
CPC ...... A61F 13/513; A61F 13/514; A61F 13/53; A61F 2013/15869; A61F 2013/49074; A61F 2013/4951; A61F 2013/4953; A61F 2013/4955; A61F 2013/4956; A61F 2013/4958; A61F 2013/51338
See application file for complete search history.

(56) References Cited

U.S. PATENT DOCUMENTS

| | | | |
|---|---|---|---|
| 2007/0088310 A1* | 4/2007 | Sugiyama ............. | A61F 13/495 604/385.19 |
| 2008/0195070 A1* | 8/2008 | Ponomarenko ....... | A61F 13/495 604/378 |
| 2010/0174263 A1* | 7/2010 | Mishima ............... | A61F 13/495 604/385.19 |
| 2010/0198180 A1* | 8/2010 | Arizti ................ | A61F 13/49017 604/385.29 |
| 2011/0184371 A1* | 7/2011 | Sakaguchi ........ | A61F 13/49473 604/385.101 |

* cited by examiner

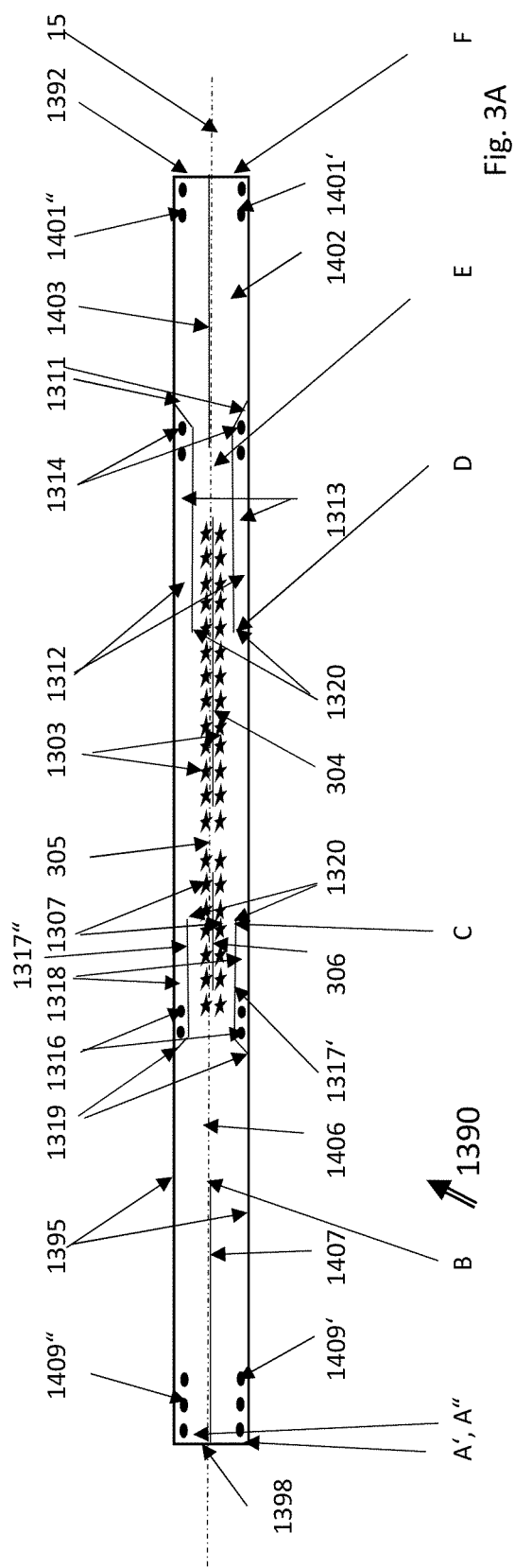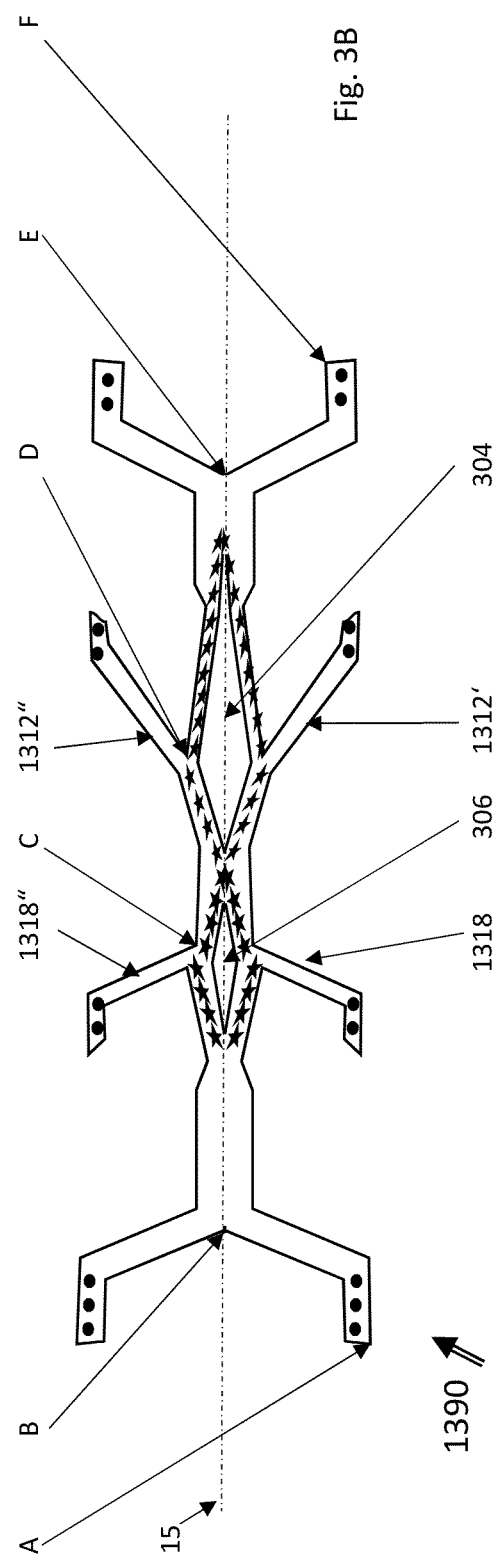

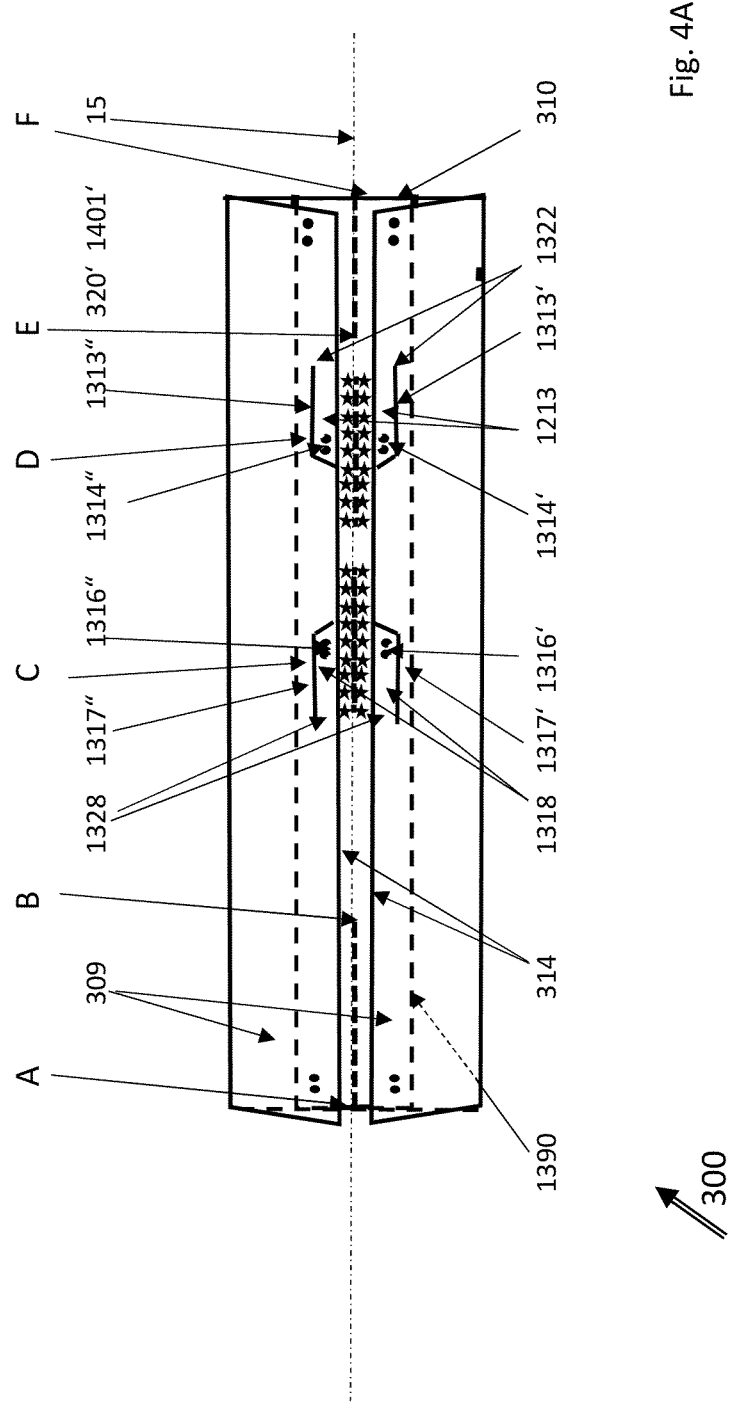

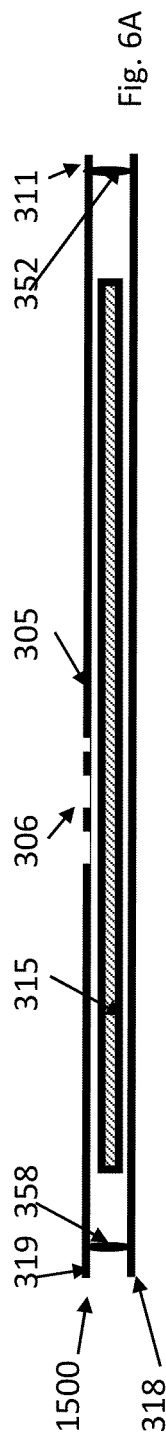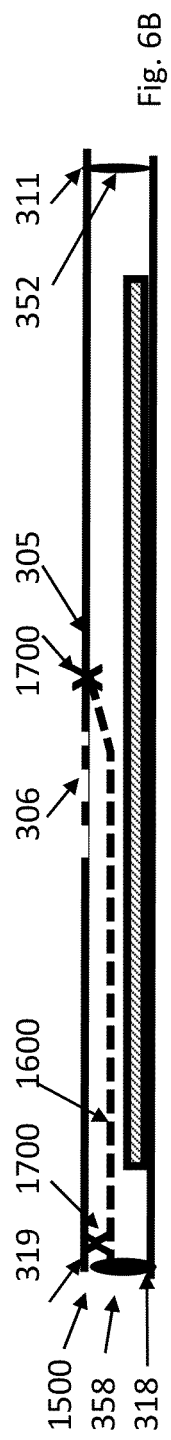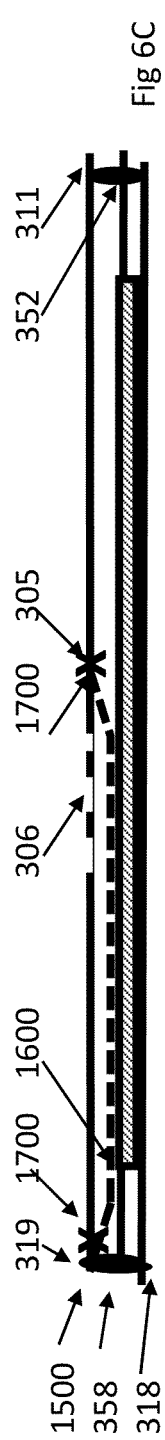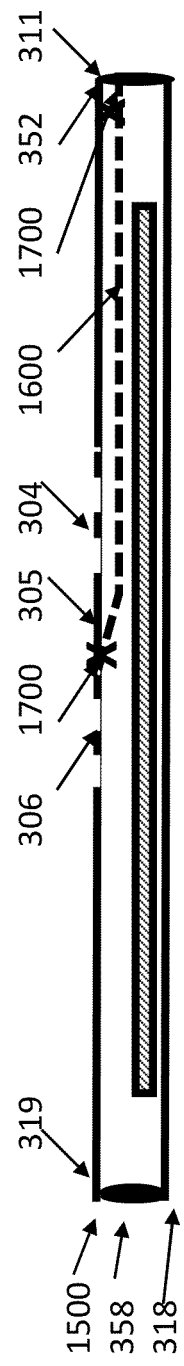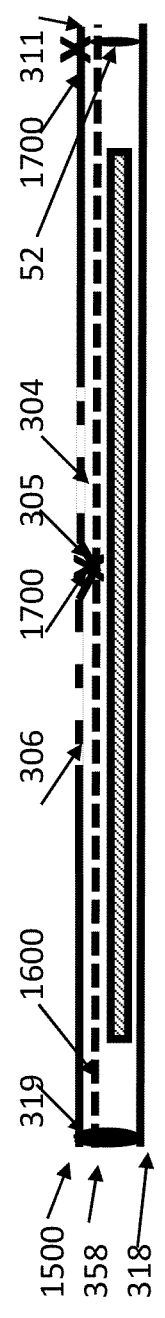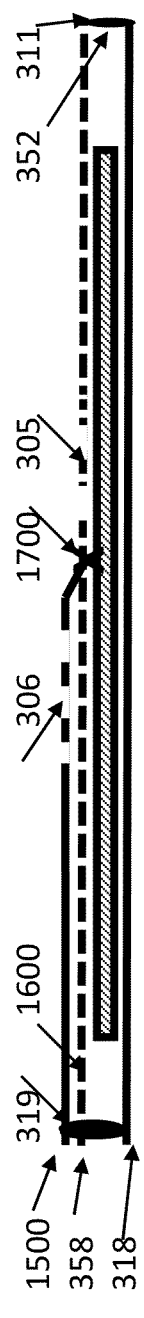

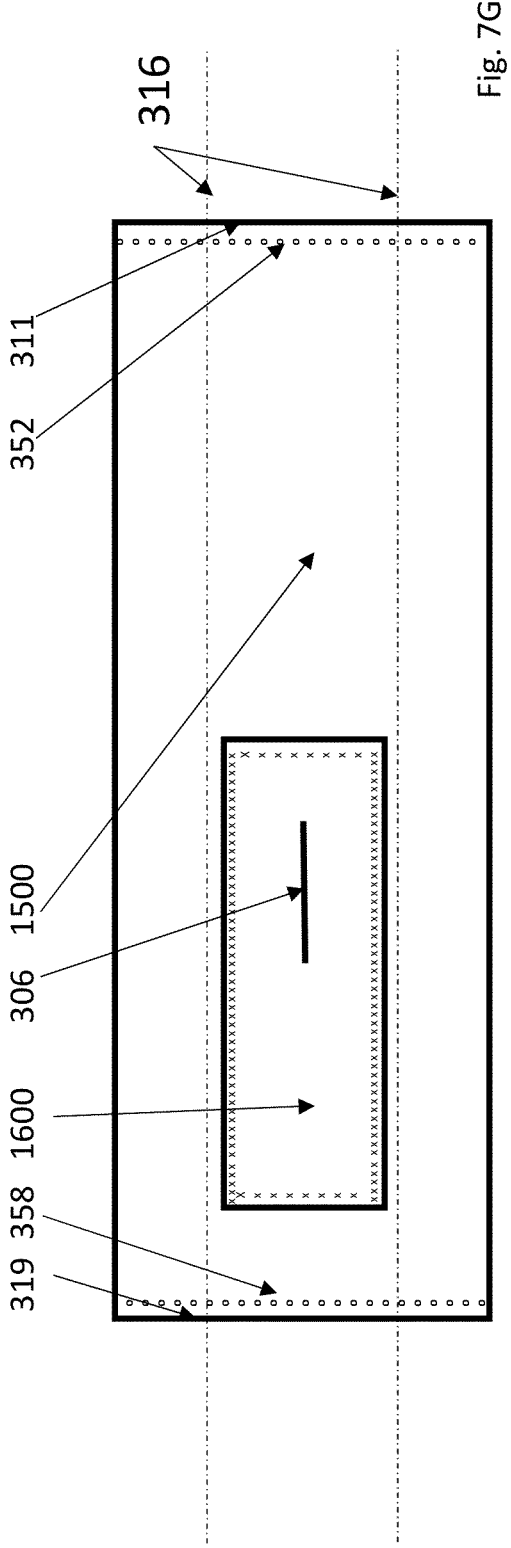
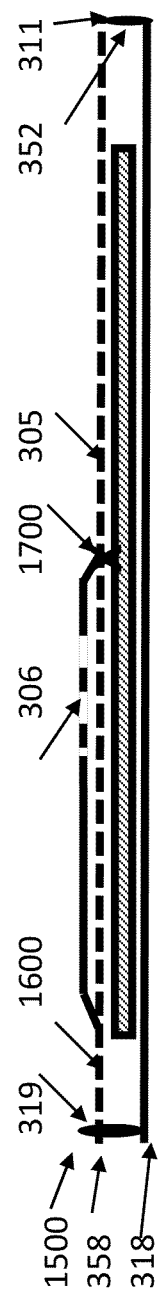
Fig. 7G
Fig. 6G

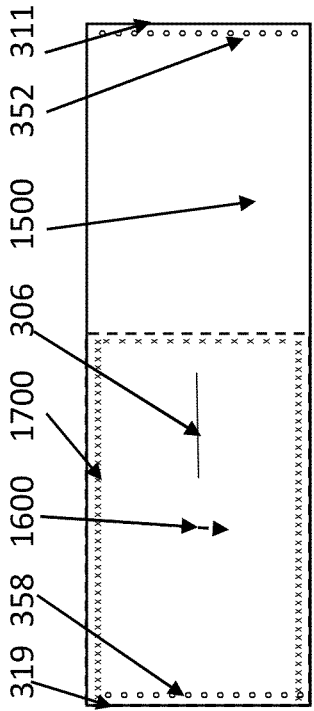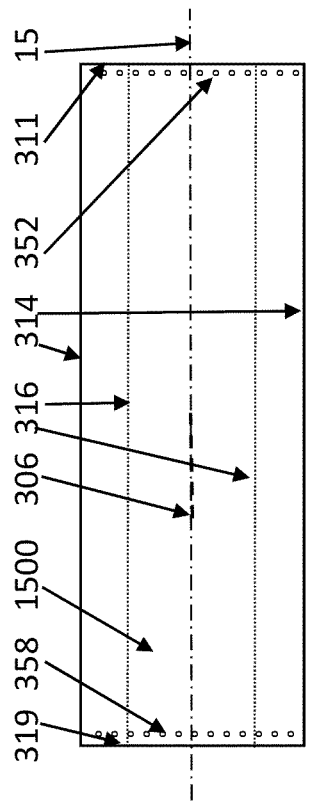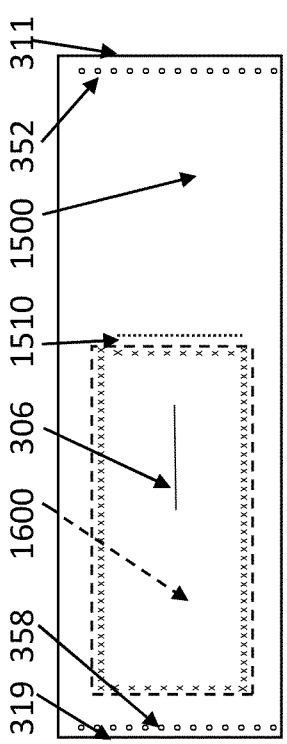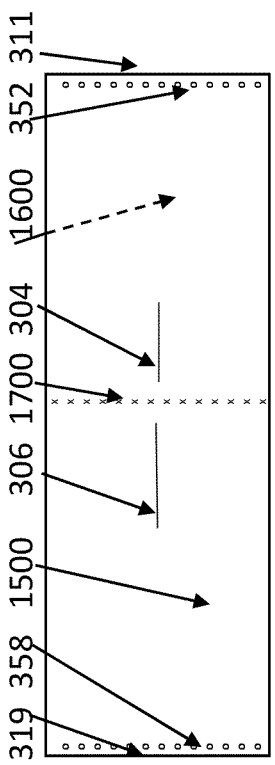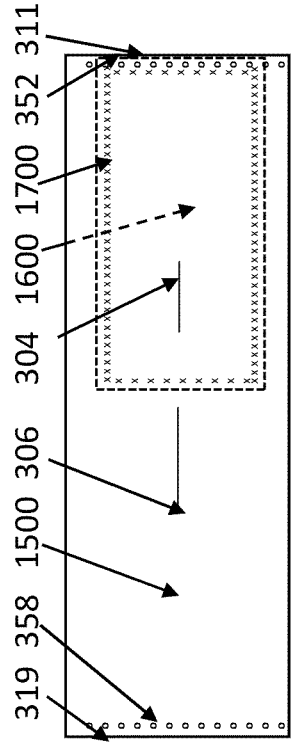

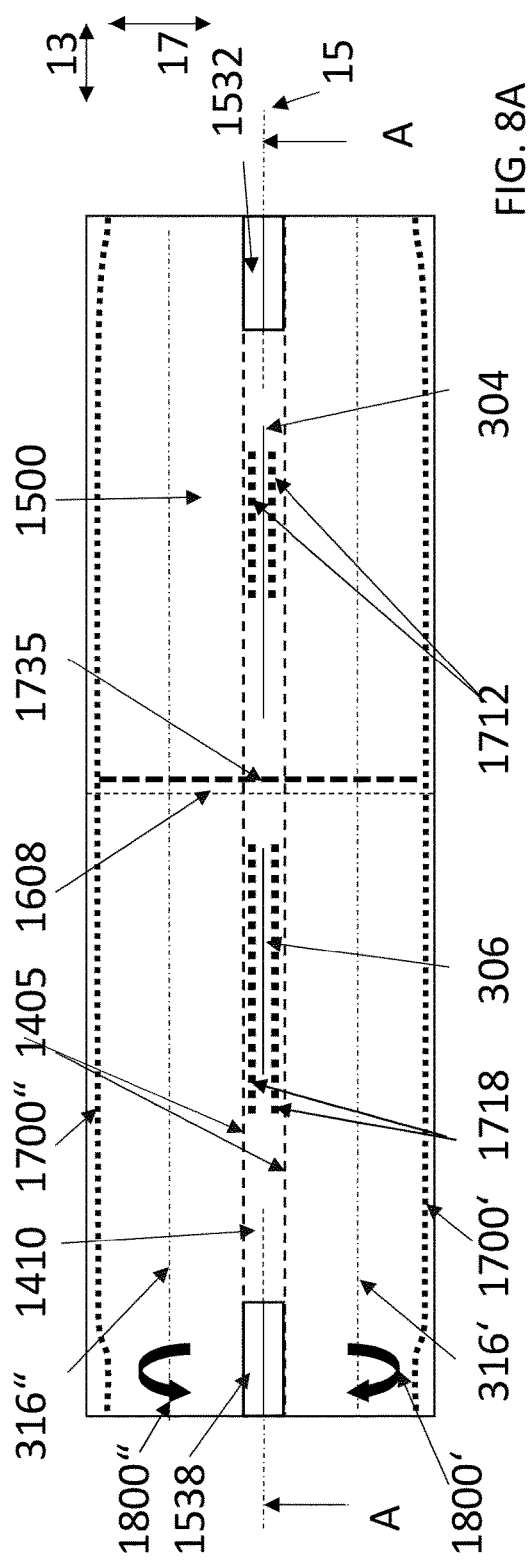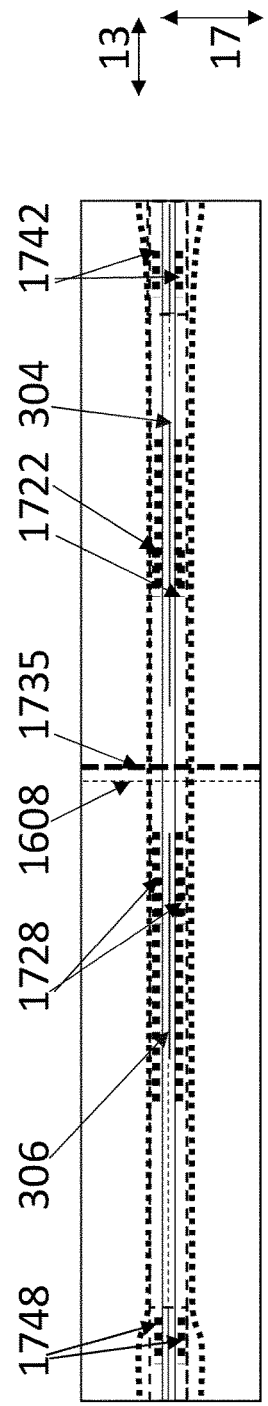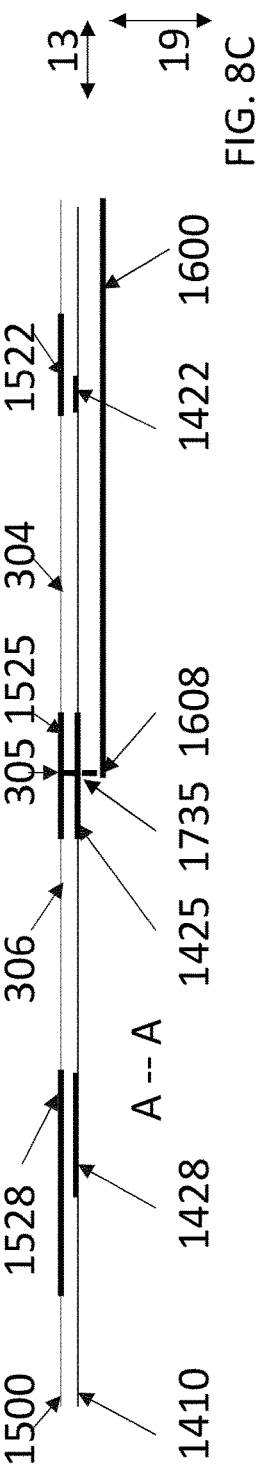

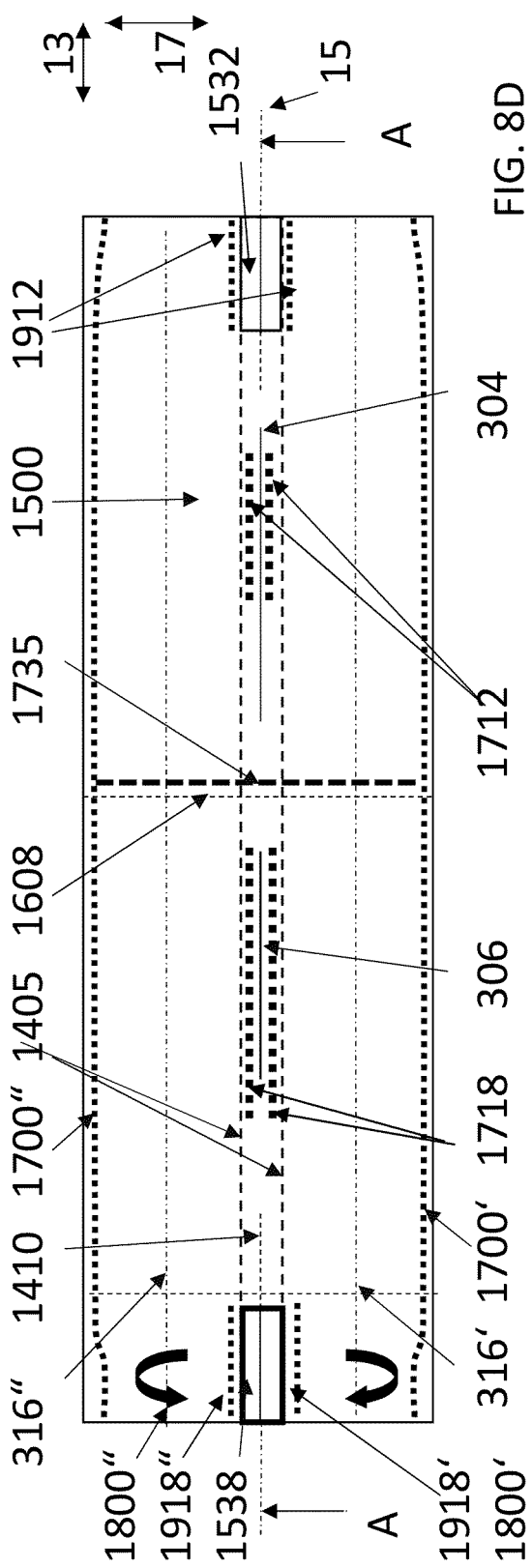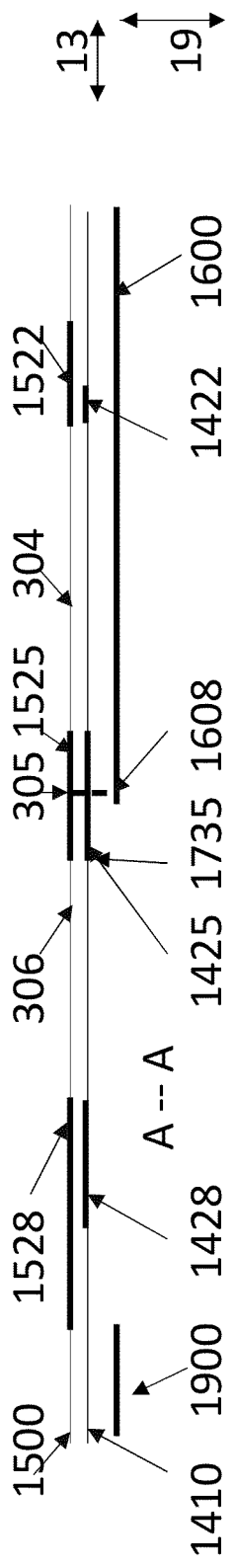

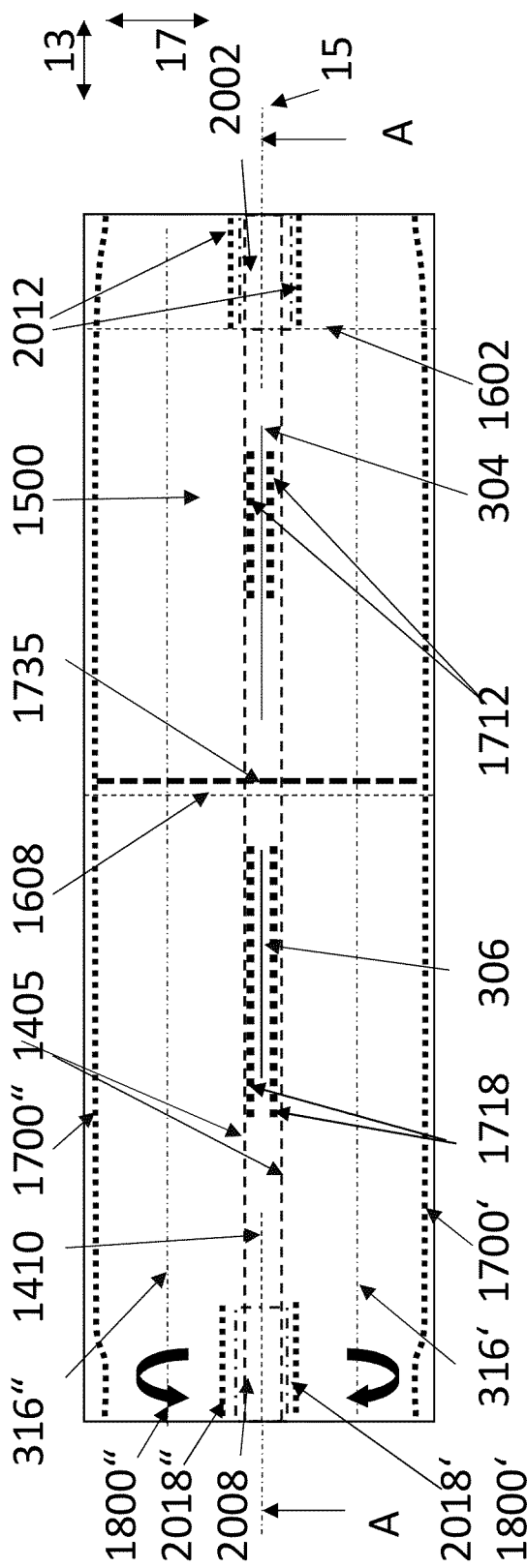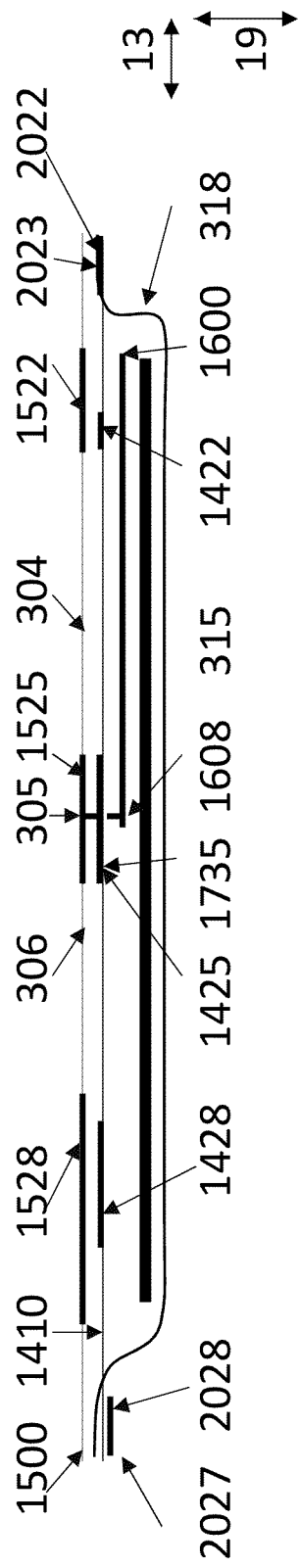

HYGIENE ARTICLE COMPRISING A SKIN PROTECTION SHEET WITH WELL POSITIONED OPENING(S)

CROSS REFERENCE TO RELATED APPLICATIONS

The present application is a U.S. National Phase Patent Application, which claims the benefit of priority from a PCT application, filed on Sep. 5, 2019, now bearing PCT Application No. PCT/EP2019/073716, which claims priority from Great Britain Application No. 1911011.3, filed on Aug. 1, 2019, Great Britain Application No. 1905408.9, filed on Apr. 17, 2019, Great Britain Application No. 1821151.6, filed on Dec. 21, 2018, and Great Britain Application No. 1814501.1, filed on Sep. 6, 2018, which are incorporated herein by reference in their entireties.

FIELD OF THE INVENTION

The present invention relates to the field of hygiene appliances, in particular to hygiene articles comprising a means for reducing soiling of the skin of a wearer by body exudates such as faeces, urine, or menses. In particular, it relates to an article with a Skin Protection Sheet that comprises at least one opening in registry with body exudate releasing body openings or genital organs, to which it is urged by a longitudinally acting pull means whilst being spread open cross-directionally by a spreading means. Such a hygiene article may suitably be a baby or adult diaper or pant, a training pant, or a menstrual pant.

BACKGROUND

There are multiple attempts to address the problem of contaminating and/or irritating the skin of a wearer especially if a wearer is unable to control bowel movement or defecation.

EP359410A1 (Freeland; P&G) discloses a disposable absorbent article with an elastic topsheet having an aperture or passageway.

U.S. Pat. No. 3,848,599A (Schaar; Kendall) shows a diaper with two parts of an absorbent core, which are positioned longitudinally partially overlapping. In the overlapping region, the topsheet follows the shingled formation, thusly forming a cross-directional fold, which is affixed at the lateral margins of the article. Thus, upon donning of the article or during use, longitudinal forces reduce the overlap in the middle portion of the article and a trough-like cavity is formed into which faeces can be deposited. In JP08-196565 (Onishi; Uni Charm) an absorbent article is described having an absorbing core with an upper layer core and a lower layer core. The upper layer core is divided in longitudinal direction and the two front and rear parts are separated by a distance. The topsheet is folded around the ends of the upper core and between the upper and lower core layer, thereby forming pockets into which faeces can be deposited.

EP908162A2 (Sayama; Uni Charm) shows a disposable diaper, wherein a supplemental member having two side walls is bonded to the top sheet and a top wall, thereby forming excreta guide openings or passageways.

US20080110553A1 (Otsubo; Uni Charm) discloses a pants-type diaper, wherein a separator sheet overlying the topsheet is connected thereto in the crotch region. Forwardly and rearwardly the separator sheet is unconnected to the topsheet in the median region. The forward and rearward longitudinal end margins of the separator sheet are connected to each other, thusly forming in an in-use configuration cone-like spaces for receiving faeces and urine, respectively.

WO2011064272A2 (Schmitz, C4S) describes an article for being worn on the lower torso of a wearer, such as pants or diapers. The article has a flexible faeces separation member, such as a faeces trap sheet comprising an opening, which is attached in a particular way such that separation of faeces and skin respective genitals can be achieved.

WO2015/055696 (Schmitz, C4S) describes absorbent articles with overfolded side margins and a faeces trap sheet with an opening, as described in the above mentioned WO2011/064272, wherein the topsheet comprising an opening and a topsheet foreshortening means is adapted such that the topsheet is in direct contact with the skin of a wearer and the opening is positioned in the region of and aligned with the anus of a wearer during use.

Whilst this provides significant improvement with regard to handling of faeces, it has been discovered that there is still a tendency for faeces to migrate rearwardly, but also, faeces can migrate forwardly towards the genitals of a wearer. It has now been identified that a cause for this remaining soiling in the previous approaches is that the topsheets and/or faeces trap sheets span over the buttocks of a wearer as well as over the genitals, and thusly are not in sufficiently close contact to the skin of a wearer, especially in the anal cleft.

It has also been recognized, that such an approach is primarily directed towards handling of faeces, whilst there is still a need for improving the handling of other body exudates, such as menses and even urine.

Thus, there is still a need for articles with improved separation of bodily exudates from the skin of a wearer by improving the contact of a separating sheet with the skin in the vicinity of the exudate releasing opening or genital organs.

There is further a need to achieve this in a simple and easy to manufacture design, with minimized amount of used material, which further should not require particular, often costly, properties, such as elasticity.

SUMMARY

The present invention is a hygiene article for being worn on the lower torso of a wearer, which comprises
- a skin protection sheet (SPS) adapted to separate bodily exudates from the skin of a wearer,
- a backsheet adapted to retain the bodily exudates,
- optionally an absorbent core adapted to absorb liquids of the bodily exudates, and
- optionally an exudate separation sheet (ESS) adapted to separate exudates from each other or from predetermined portions of the article.

At least the SPS comprises at least one opening adapted to be positioned in registry with a bodily exudate releasing body opening or a genital organ. The article further comprises a pull means adapted to urge the SPS into the anal cleft of a wearer during the article's intended use, and spreading means adapted to maintain at least one of the opening(s) cross-directionally open during the article's intended use.

A hygiene article according the present invention may be worn on the lower torso of a wearer and be adapted to receive and retain bodily exudates. The article exhibits a length/longitudinal/x-direction, a width/cross-directional/y-direction, perpendicular thereto and corresponding to a left-right orientation of a user during its intended use, a thickness/z-direction, perpendicular to both, and a longitudinally extending center line.

During its intended use, the article comprises, relative to a wearer, a rear waist region and a front waist region, each comprising cross-directionally opposite first and second side panel sections and a center section there between, and a crotch point region positioned longitudinally between the waist regions, and comprising a crotch point positioned between the anal opening and the genital organs of a wearer.

The article is adapted to be converted from a manufacturing configuration into an in-use configuration, wherein the hygiene article adopts a general U-shape along the longitudinally extending center line extending from the front or rear waist region of a wearer through the crotch point region into the opposite waist region of the wearer, and wherein the front and rear waist regions are adapted to encircle the waist of a wearer.

The article comprises a skin protection sheet (SPS) comprising an outer SPS surface intended to be in direct contact with the skin of a wearer at least in portions of at least one of the front and rear waist portions and an opposite SPS surface. The SPS comprises at least one SPS opening adapted to be in an in-use configuration in registry with a bodily exudate releasing body opening or a genital organ and is extending from the front or the rear waist regions at least into the crotch point region of the article, optionally into the opposite waist region;

The article may optionally comprise an Exudate Separation Sheet (ESS) positioned z-directionally towards the opposite SPS surface, being connected to the SPS directly or indirectly at least in the crotch point region and extending from the crotch point region towards at least one of the front and rear waist regions.

The article further comprises a longitudinal foreshortening pull means (PM), a cross-directional spreading means (SM), a backsheet (BS) adapted to retain bodily exudates in the article positioned opposite of the outer surface of the SPS, side panels (SP) extending laterally outwardly of the SPS at least in an in-use configuration, and optionally an absorbent core positioned z-directionally between the SPS and the backsheet. The absorbent core may comprise liquid absorbent material and at least partially liquid permeable envelope web(s). The combinations of certain elements may form precursor or precursor webs, such as the absorbent core or a center piece comprising at least a BS and side panels, that may be unitary with the backsheet or separate and connected thereto.

In the manufacturing configuration, at least one of the SPS and the ESS comprise(s) longitudinal side margins that are overfolded along a longitudinal fold line towards but not over the longitudinal center line of the article. Further, the pull means is positioned essentially along the longitudinally extending center line and against the upper or opposite surface of the SPS. Thereby, the PM extends from at least one of the cross-directionally extending margins in the front or rear waist region of the SPS or ESS towards the crotch point, optionally further towards or into the opposite waist region, and if then covering the opening(s) of the SPS, further comprises (a) pull means opening(s) in registry with the opening(s) of the SPS. In a preferred execution, the PM is then connected in the front or rear waist regions to the overfolded portions of the SPS or ESS. In addition, the pull means comprises a longitudinally extending waist separation line aligned with the longitudinally extending center line of the article, and extending from the front or rear waist regions towards but not into the at least one opening of the SPS. If the PM extends into the opening(s), it further comprises pull means opening(s) in registry with the SPS opening(s).

The spreading means of the article is selected from the group consisting of
  a connection of the overfolded portions of the SPS or ESS to the outer surface of the SPS or PM laterally outwardly of the opening;
  a pull means strip partially cut from the pull means by a separation line extending from and intersecting a longitudinal side margin of the pull means towards but terminating at a termination point before intersecting the pull-means opening, whereby the intersection of the longitudinally extending side margin is distanced further away from the crotch point than the termination point of the separation line and connected at its laterally outward end to the overfolded portions of the SPS or ESS; and
  an overfold strip, partially cut from the overfolded portion of the SPS or ESS by a separation line extending from and intersecting a longitudinal overfolded side margin of the SPS or ESS towards a termination point laterally outwardly of the opening, whereby the intersection of the longitudinally extending side margin is distanced less far away from the crotch point than the termination point;
  a reinforcement means in the peripheral region of the opening.

In an in-use configuration, the SPS is lifted z-directionally and adapted to fit into the anal cleft of a wearer by the PM, and the at least one opening of the SPS is cross-directionally maintained open by the SM.

When the overfolded strip is partially cut from the overfolded portion of the SPS or ESS by a separation line, the termination point is positioned such that it z-directionally overlays the PM or the SPS.

Preferably, the ESS may be selected from the group consisting of hydrophilized nonwoven material, hydrophobic nonwovens, films, and apertured films, or combinations thereof.

For a hygiene article according to the present invention in a manufacturing configuration, the PM exhibits a cross-directional extension that is larger than the cross-directional distance of the overfolded longitudinal extending side margins of the center piece, whereby the SPS or the ESS is connecting to the upper surface of the PM or SPS in the proximity of the at least one discontinuity.

Optionally, and for certain executions preferably, at least the SPS, PM, SM are essentially non-elastic.

For the hygiene article according to the present invention, a precursor may—in a manufacturing configuration—exhibit an overall article length corresponding to the one of the article in a manufacturing configuration and comprise sections that are separated by characteristic points along the longitudinal center line, wherein the distances between the characteristic points exhibit the following ranges, whereby the specific point A to F are discussed in more detail herein below:
  from the rear waist margin (point A) to the forward end of the waist separation line (point B): 10% to 25%;
  from the forward end of the separation line (point B) to the midpoint point of the rear discontinuity (point C): 20% to 40%;
  from the midpoint point of the rear discontinuity (point C) to the midpoint point of the front discontinuity (point D): 15% to 25%;

from the midpoint point of the front discontinuity (point D) to the rearward end of the front waist separation line (point E) to the front: 5% to 25%;

from the rearward end of the front waist separation line (point E) to the front waist margin (point F): 10% to 25%, whereby the respective percentage figures should add up to 100% corresponding to the overall article length and whereby, when certain features a not present, the distances are counted to the next characteristic point.

A hygiene article according to the present invention may be an absorbent article, selected from the group consisting of baby diapers, adult incontinence article and feminine hygiene article.

In another aspect, the present invention is a process for the manufacture of a hygiene article, which comprises the following steps not necessarily in the following order:

providing
- a center piece web comprising
  - a backsheet web, preferably a liquid impermeable web,
  - side panels, which are integral with the backsheet web or provided as separate web material, preferably as a breathable web,
- a web material for a skin protection sheet (SPS),
- a web material for a pull means (PM), optionally being unitary with or comprising a spreading means (SM), then forming a combined pull and spreading means (CPSM), and
- glue;

applying waist separation lines to the PM web and optionally PM spreading strip separation lines;

applying a rear or front separation line to the SPS web;

separating pieces of predetermined length from the PM web and combining these with the SPS web;

separating pieces of predetermined length from the combined PM-SPS web and combining these with the center piece, whereby preferably the predetermined length of the separated pieces from the combined PM-SPS corresponds to the length of the center piece;

applying glue to the flat PM-SPS-center-piece composite;

overfolding longitudinal side margins of the flat article precursor and connecting the overfolded portions, preferably by glue, to the SPS or PM;

separating the overfolded flat article precursor into individual articles.

The process may further comprise one or more of the process steps—not necessarily in the following order—selected from the group consisting of:

providing an ESS web material;
providing spreading means
- as partially separated spreading means strips
  - from the CPSM material or
  - from lateral side margins corresponding to the longitudinally overfolded portions of the center piece; or
- by connecting the longitudinally overfolded portions of the center piece to the user oriented surface of the SPS or PM adjacently to the separation line for forming the opening;
- by applying a reinforcement to the opening;

applying longitudinal separation lines to the PM web material as waist separation lines along the longitudinal center line such that these extend after combination with the center piece away from the front or rear margin, but not over the full length of the pull means;

applying a cutout in the rear and/or front waist regions of the SPS or BS applying glue to the SPS and/or the PM at the periphery of the separation lines that correspond to the rear or front opening;

applying a separation line for front and or rear openings to the SPS and the PM, preferably simultaneously;

providing an exudate separation sheet (ESS) web material and connecting this to the SPS at least in the region corresponding to the crotch point region along an essentially cross-directionally extending connection;

providing side closure means adapted to connect respective front and rear portion of the side panels.

providing fixation means on the upper or opposite surface of the PM in at least one of the front or waist regions.

Preferably, the connecting of material webs or pieces separated therefrom to further material webs or pieces separated therefrom is executed by melt-fusion bonding, preferably ultrasonic bonding, unless it interferes with other webs or pieces that are z-directionally stacked but intended to remain unconnected in this bonding region.

BRIEF DESCRIPTION OF THE FIGURES

FIG. 3A to D depict particular elements suitable for the present invention and its inclusion into a hygiene product.

FIGS. 6 A to G and 7 A to G depict further particular elements according to the present invention.

Same numerals in various figures refer to the same elements or features. Figures are schematically only and not scaled.

DETAILED DESCRIPTION

Figure 2A:
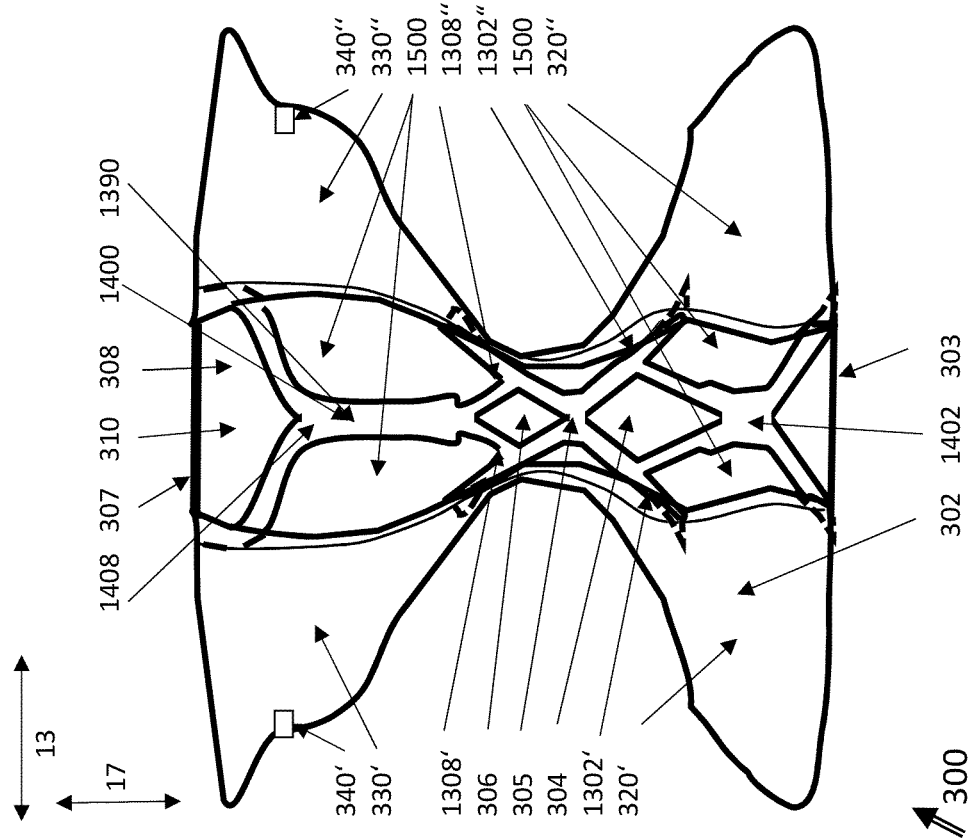
FIG. 2A to C depict an execution of articles according to the present invention and its fit on the lower torso of a wearer.

The present invention relates to a hygiene article comprising a skin protection sheet, hereinafter abbreviated as "SPS". Such an article of manufacture is typically applied to the lower torso of a human, aiming at reducing soiling of the skin by body exudates, such as during menstruation or when a wearer is not able to control urination or bowel movement.

Such hygiene articles further comprise a backsheet that retains the body exudates and prevents soiling of the environment, such as clothing or bedding. Often such articles also exhibit liquid absorbency. Optionally, a hygiene article according to the present invention may comprise an exudate separation sheet (ESS), which may separate exudates from each other, such as when contact of urine and faeces should be prevented, or from predetermined portions of the article, such as when a portion particularly adapted to receive urine should not be contaminated by faeces that may impede urine absorption. Thus suitable hygiene articles may be diapers for babies or adults, be these of the "open type" with closure means such as tapes, or be these of the "pants type" closed at the sides so as to create a belt like system around the waist, training pants or fixation pants made of film or other materials. Suitable hygiene articles include diapers in an "all-in-one" execution, i.e. with combined liquid absorbency and liquid impermeable cover, or "two-piece", i.e., separate means for addressing liquid absorbency and liquid barrier function, or "inserts", wherein an absorbent article may be equipped with a replaceable absorbent pad. Other two-piece executions include the combination of an absorbent pad with fixation mean, such as a stretchable cover, such as a net pant. An article according to the present invention may also be used in combination with a conventional absorbent diaper or pant, e.g. to enhance bowel movement handling.

Hygiene articles may be disposable, i.e. discarded and/or further treated in an environmentally friendly and sound manner and may also be made from or comprise re-usable materials.

A hygiene article according to the present invention can be in a "manufacturing configuration" which refers to a state of being produced in a manufacturing system, preferably a high speed manufacturing system, allowing to produce more than hundred pieces per minute, more than 300 pieces per minute even more than 600 pieces per minute or even more than 1000 pieces per minute. At the end of the manufacturing line, the hygiene article may be brought into a "packaging configuration", such as by being cut and folded, in which it is delivered to a user, as may be the wearer or a caretaker, who will then bring the article into a "pre-use configuration" such as by unfolding it. Upon donning on a wearer, the article takes an "in-use configuration". The SPS may be combined with a hygiene article precursor at the manufacturing stage, or by a user e.g. when establishing the "pre-use configuration". Typically, an absorbent article exhibits a width or cross-direction or y-direction, corresponding to a left-right orientation of a user during its intended use. Further, the length, longitudinal or x-direction of the article extends perpendicularly thereto, and in an in-use configuration from a first waist region, e.g. the rear waist region, through the crotch region to the opposite waist region, whereby the respective regions of the article correspond to the body regions of a wearer. Thus, in this in-use configuration the longitudinal center line of an article will take a U-shape configuration, whilst in a manufacturing configuration the longitudinal center line is often a straight line. Further, the article exhibits a thickness or z-direction, perpendicular to the x-, and y-directions. The overall length of the article in an in-use configuration corresponds to the outermost line of the article, which is the backsheet as described below, following this U-shape, thus stretching from the rear waist margin of the article through the crotch region to the front waist margin. In a manufacturing configuration, where individual articles are not yet separated but represent an essentially endless sequence of connected article precursors, the overall length of an article is considered to correspond to the distance of marked-up or imaginary lines where the articles are separated from adjacent ones towards the end of the manufacturing process.

Figure 1:
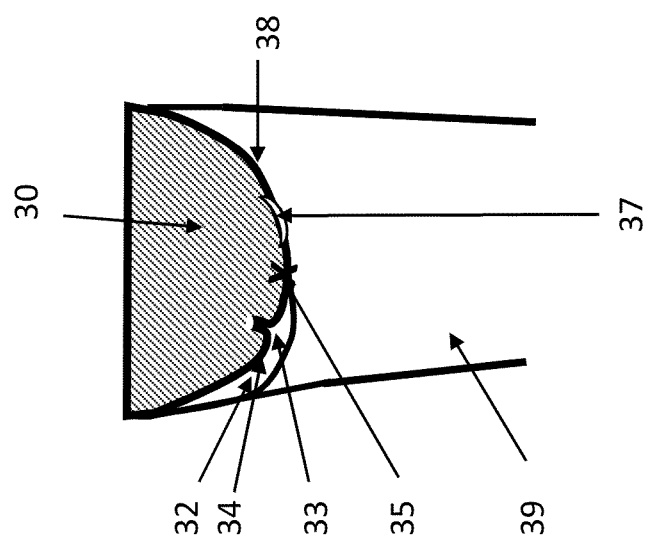
FIG. 1 depicts the lower torso of a wearer to which an article according to the present invention may be donned.

The principles of the present invention are now explained by referring to the figures, which should not be seen to be limiting, in particular not with regard to combining various features as described as exemplary executions. FIG. 1 depicts schematically a portion of the sagittal plane of a body, with lower torso 30, upper thigh of a leg 39 and buttocks 32, the latter being separated by the anal cleft 34. Further indicated are the anus 33 and the genital organs, here shown as labium 37, which is also the location of the male genital organs, scrotum and penis. Left and right groin clefts 38 extend from the crotch region forwardly. The perineum with a crotch point 35 is the region between anus and genital organs. The length of the perineal region has a person to person variability, and is also somewhat dependent on the gender and age. Typically, a range of 2.5 cm and 7 cm covers most of the adults, with a medium length of between 4 cm and 5 cm, both ranges being applicable to female and male persons. For Babies, the perineal length is typically shorter, though not below about 1 cm. Thus, typically, the crotch point on a wearer is positioned between about 0.5 cm and about 4 cm forwardly of the forward end of the anus.

Within the present invention, the crotch point of an article 305 corresponding to the crotch point of a wearer 35 can be determined by placing an article on a wearer of the physical size for which the article is designed and who is in a fully upright standing position with his or her feet a shoulder width apart and then placing an extensible filament around the upper thighs in a figure eight configuration. The point in the article corresponding to the point of intersection of the filament is considered to be the crotch point of the article. Further, the crotch point region of an article is longitudinally extending forward and rearward of the crotch point corresponding to the perineal region of a wearer. In absence of concrete figures for a particular user, the crotch point region is considered to extend at least 1 cm forward and rearward of the crotch point.

Figure 2C:
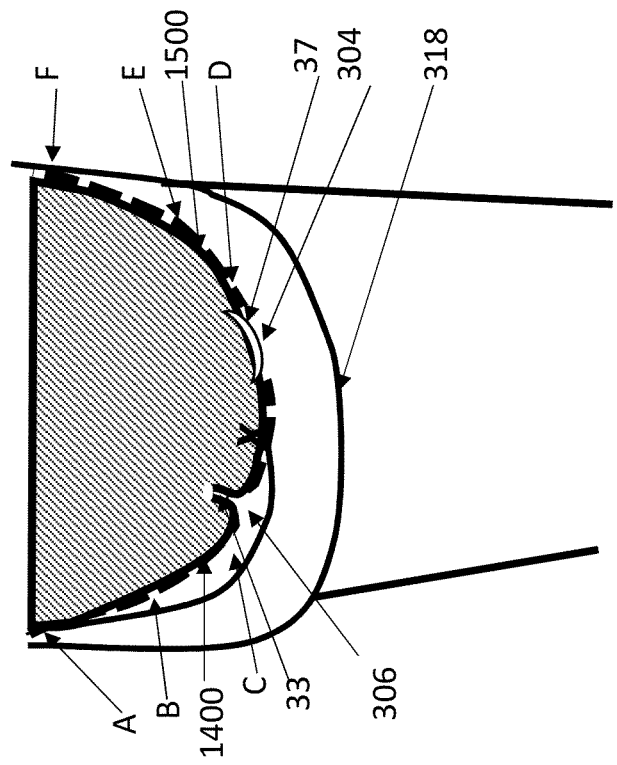
Figure 2B:
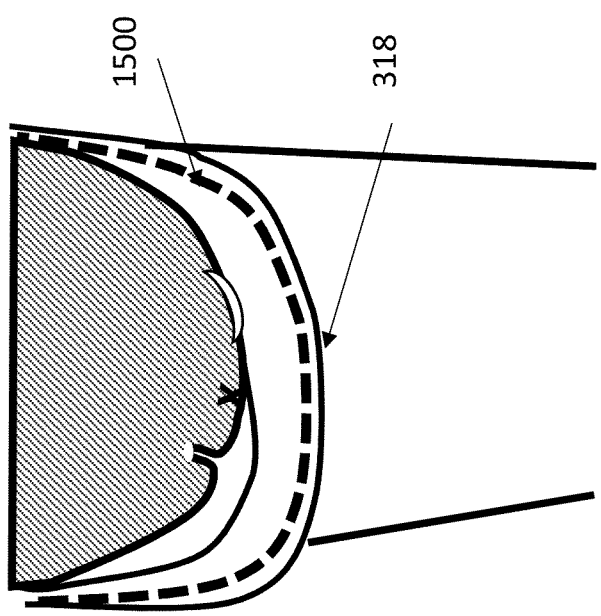

In order to explain the general functioning of the present invention, reference is made to FIG. 2A to 2C. FIG. 2A depicts schematically and non-limiting a top view of an execution of article 300 according to the present invention in a pre-use configuration, with longitudinal direction 13 and width direction 17. The article 300 comprises a front region 302 with front cross-directionally extending margin 303 and a rear region 308 with rear cross-directionally extending margin 307 and a crotch region 305 longitudinally there between. Further, front side panels 320' and 320" and rear side panels 330' and 330" extend laterally outwardly from a center piece 310. The side panels may be separate materials as connected to the backsheet material, or they may be lateral extensions of the backsheet material.

When reference is made to features, that are essentially symmetric to a longitudinal center line, as may be a "left-right" symmetry for an article, here shown for the side panels, the respective "left" or "right" features are denoted with single and double quotation marks, respectively, whilst in a general discussion of the feature, no quotation mark is used. The side panels may comprise closure means 340' and 340" that allow fitting of the article around the waist of a wearer by connecting front and rear side panels, respectively. As most of the materials suitable for being used in the present invention are essentially flat or web materials, they generally exhibit two surfaces separated by the thickness. Within the present context, a first surface of the materials is generally oriented towards the wearer and the second or opposite surface away from the wearer or outwardly, at least in the crotch region, and even if certain portions of the materials are overfolded or are positioned towards the legs of a wearer.

In this exemplary execution, the article 300 further comprises a rear or anal opening 306 and a front or genital opening 304, both being cross-directionally spread open by spreading means (SM) 1300. As will be discussed in more detail herein below, each of the spreading means comprises a pair of spreading elements, here shown for the front, 1302' and 1302", and the rear 1308', 1308". Pull means (PM) generally depicted as 1400, here shown as a pull means strip 1410 with a rear pull means 1408 and a front pull means 1402, are indicated as exhibiting a Y-shape, with the stem of the "Y" directed towards the openings 306 and 304, respectively, and the legs of the "Y" directing away from the opening and laterally outward. As shown, the pull means and the spreading means may be unitary, e.g. by being made of a single piece of material. A Skin Protection Sheet (SPS) 1500 is shown in the region of the center piece 310 except for the openings.

FIG. 2B depicts the portion of the sagittal plane of a body as in FIG. 1 with an article in a pre-use configuration as shown in FIG. 2A with the side panels not being fully outwardly folded and openings, PM, and SM omitted. The SPS 1500 and the backsheet 318 exhibit essentially the same longitudinal extension. Upon donning, and as depicted in FIG. 2C, the outward folding of the sidepanels for closure of the article around the waist pulls the front and rear ends of the legs of the Y-shaped pull means 1402 and 1408 laterally outward, thusly foreshortening the available longitudinal extension, and thusly urging the pull means 1400 as well as the SPS 1500 connected thereto into the anal cleft such that the openings are also urged towards the anus and genital organs whilst the backsheet remains spaced apart. At the same time, the spreading means induce a lateral pull to the openings thereby widening their CD-extension at predetermined size, such that the rear opening fits tightly to the anus and the front opening is adapted to allow the genital organs to pass through. Thus exudates pass through the openings into the space created between the SPS and the backsheet, separated from the skin by the SPS.

FIGS. 3A and B now refer to features of the pull means 1400 and spreading means 1300, as indicated in the above in the context of FIG. 2 for the particular execution of these being unitary, i.e. made of a single piece of material, as may be referred to as Combined Pull and Spreading Means CPSM 1390. In FIG. 3A it is shown in a manufacturing configuration, whilst FIG. 3B depicts schematically an in-use configuration (not showing the three-dimensional U-shape), with a view on the wearer oriented first surface. A simple strip of skin friendly material, such as conventional nonwoven material of sufficient strength is provided with a plurality of discontinuities or separation lines, such as may be full cut lines or tear open lines ("perf'n pop). It is further contemplated though less preferred, that the spreading means may be introduced as a separate material strip.

Front (1402) and rear (1408) pull means comprise discontinuities 1403, 1407, respectively, that extend from the front (1392), respective rear (1398) margins of the CPSM, also indicated by point F and A, respectively, and coinciding with the front and rear margins of the article (shown in FIG. 2A, 303 and 307, respectively). The discontinuities stretch towards the crotch point 305 and stop at points E and B, respectively, corresponding to the node points of the Y-structures described in the above. The stems of the Y-structures, 1404 and 1406, respectively, further extend from the node points E and B in the direction towards the crotch point up to the discontinuities for the openings 304 and 306. These discontinuities extend further in the direction towards the crotch point 305, but will not reach there, such that an unseparated region remains in the crotch point region.

For the exemplary execution as shown in FIGS. 2 and 3, spreading means 1300 are executed as pairs of partially separated strips 1312' and 1312" for the front opening 304, and 1318' and 1318" for the rear opening 306. These strips are partially separated from the CPSM material by separation lines 1313, 1317, that extend from and intersect a longitudinal side margin 1395', 1395" of the CPSM towards but terminating before intersecting the discontinuity for the openings 304, 306, respectively, whereby the intersection with the longitudinally extending side margins and thus the laterally outward end portions 1311', 1311", 1319', 1319" of the spreading means strips 1312, 1218 are distanced further away from the crotch point 305 than the termination points C and D that are positioned just laterally outwardly of the openings and about midways of the length of the respective discontinuities (as indicated for point C) or more towards the crotch point (as indicated for point D). In addition to these discontinuities, the CPSM comprises connection points for connecting to other elements of the hygiene article.

As to the pull means function, the front pull means connecting regions 1401', 1401" near the front margin 1412 and corresponding to point F, and the rear pull means connecting regions 1409', 1409" near the rear margin 1418 and corresponding to point A are positioned laterally outward of the discontinuities 1403 and 1407, respectively, and connect to overfolded portions of the center piece and to the side panels, as will be discussed in more detail herein below.

Similarly, the spreading function is enabled by connecting the laterally outward end portions 1311', 1311", 1319', 1319" in respective connecting regions 1314', 1314", 1316', 1316" to overfolded portions of the center piece and to the side panels, as will be discussed in more detail herein below. Further, the peripheries of the discontinuities forming opening 304 and 306 are connected to the underlying portion of the SPS, which comprises corresponding discontinuities, as will also be discussed herein below.

Figure 3C:
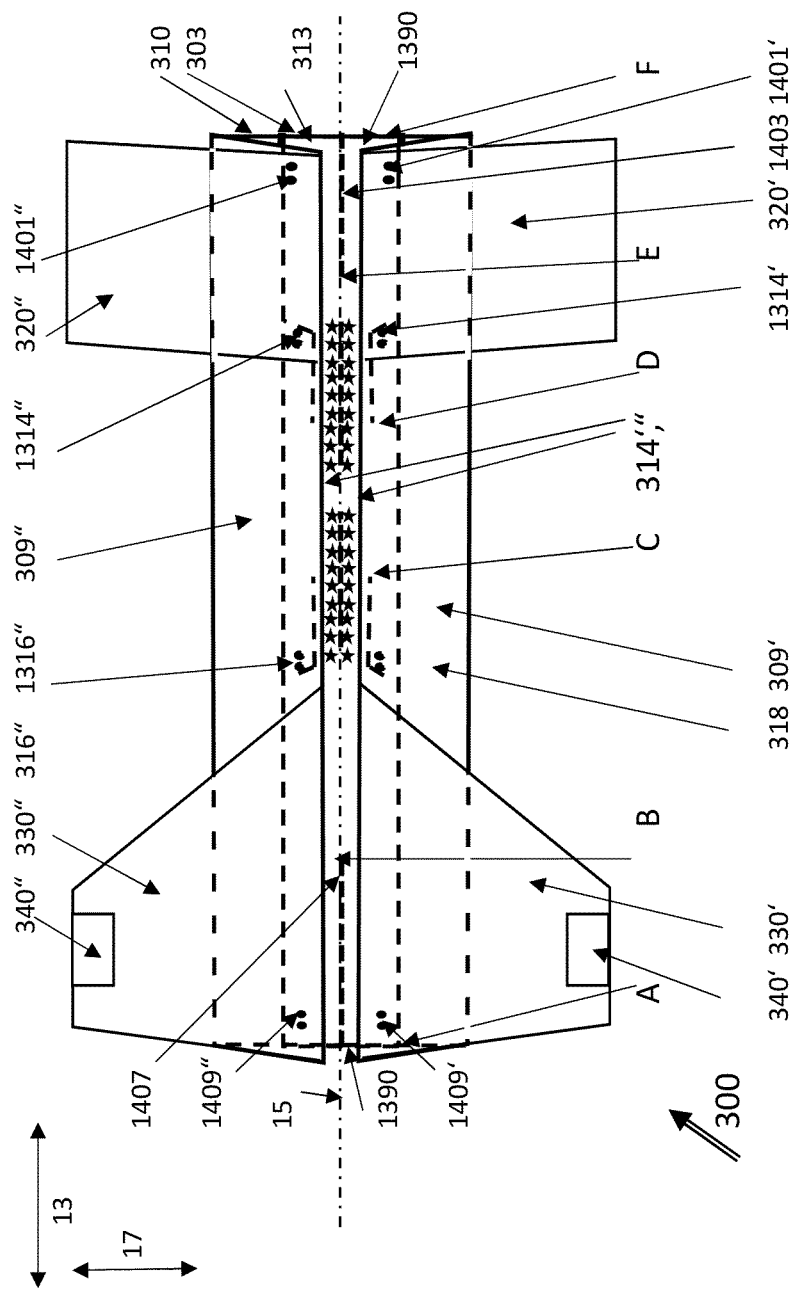
Figure 3D:
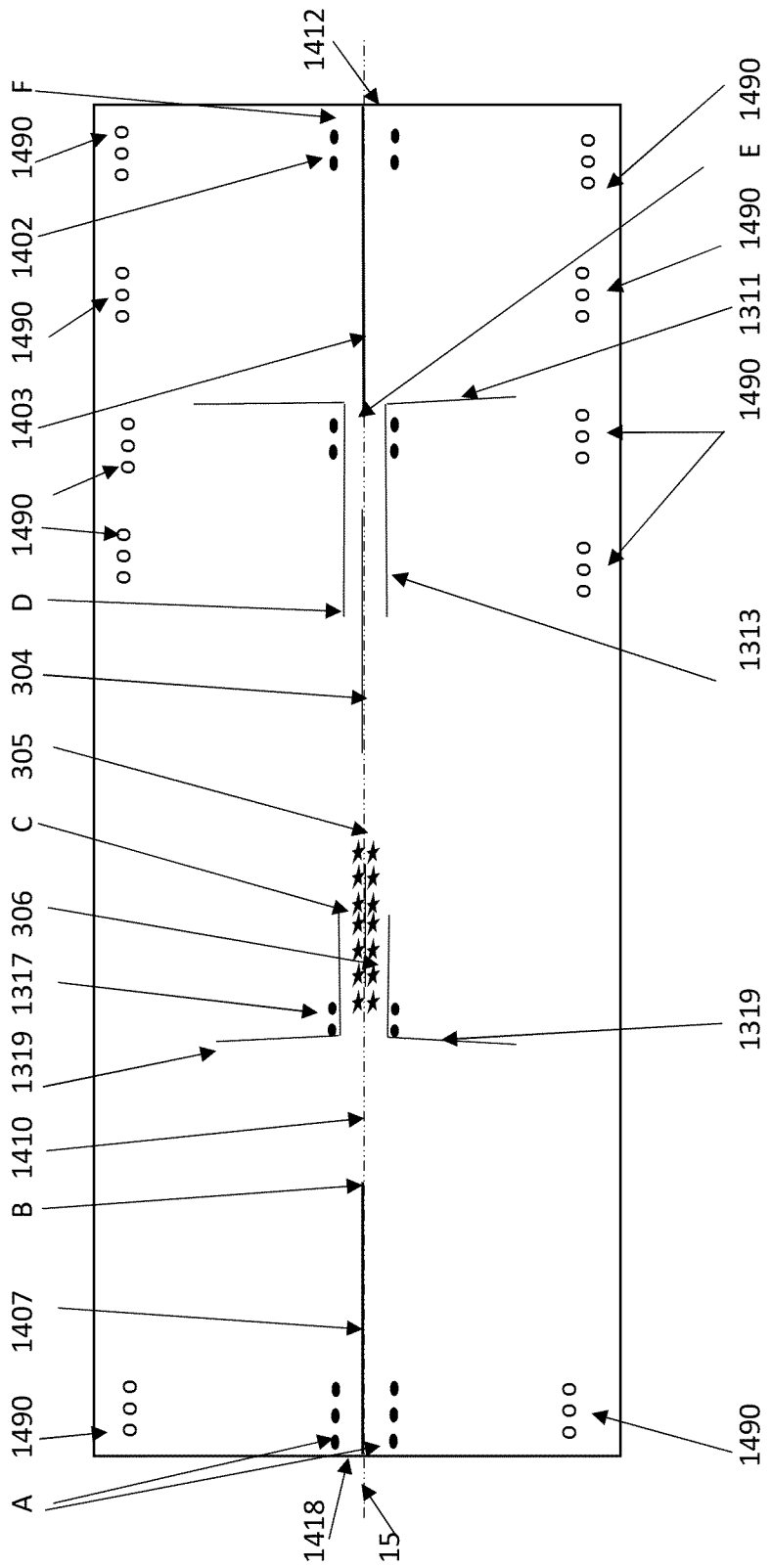

As indicated in FIG. 3C, a hygiene article 300 comprising a CPSM 1390 is shown in a manufacturing configuration, corresponding to an article as shown in FIG. 2A in a pre-use configuration. The exemplary article comprises a front side panels 320', 320", rear side panels 330', 330" with closure means 340', 340". and a center piece 310. The center piece 310 comprises at least a SPS sheet 1512 as described in the above, and a backsheet 318, typically, though not necessarily an absorbent core (not shown), and exhibits an overfolded "C-shape", with longitudinally extending side margins 314', 314" that are overfolded along longitudinal fold lines 316', 316" towards but not over the longitudinal center line 15 of the article, such that in the overfolded portions 309 the backsheet 318 faces the viewer. The center piece 310 exhibits a first surface 313, as may also be referred to as topsheet side, that apart from overfolded regions generally faces towards a wearer in the in-use configuration, and in the manufacturing configuration of FIG. 3C it is merely visible at the front margin 303. In the execution as exemplarily shown in FIGS. 2 and 3, this surface is of the SPS as described above. The side panels are connected to these overfolded portions in proximity of the longitudinal side margins 314, and may—in another variant of a manufacturing configuration—also be downwardly folded around the longitudinal fold line of the center piece, such that this manufacturing configuration is essentially rectangular.

An article may further comprise various other functional or aesthetic elements, such as side panel extensions, barrier leg cuffs, leg hoops, leg elastics, waist elastics, landing zones and related fasteners, lotions, printing, and other elements as used in products currently available for purchase, all well known as such in the art.

The CPSM strip 1390 is positioned on the first surface of the center piece or to the second surface of the SPS prior to the execution of the overfolding, with the separation lines 1313, 1317, 1403, 1407 cut or otherwise applied thereto as described in the above. Connecting means such as glue or melt-fusion bonding dots or lines can be applied to connecting regions 1303, 1307 in the periphery of the discontinuities for the openings 304 and 306 onto the first surface 313 of the center piece or the corresponding regions of the CPSM, i.e. opposite of the user oriented surface 1397 of the CPSM, such that when the CPSM is placed onto the center piece the connection is established, optionally enhanced by compression, e.g., by pressure roller. Further, connecting means such as glue dots or lines can be applied to connecting regions 1314, 1316, 1401, 1409, or to the corresponding regions on the first surface of the center piece, such that upon overfolding the connection is established, optionally enhanced by compression, e.g., by pressure roller. Thus, in this manufacturing configuration, the CPSM is connected to the center piece in central portions in the periphery of openings 304 and 306, that are in registry in the SPS and the CPSM, and along the longitudinal side margins of the overfolded portions.

The principles of the present invention can now be explained by considering the conversion from the manufacturing configuration, see FIGS. 3A and C to a pre-use configuration as in FIGS. 2A and B to an in use-configuration as shown in a simplified view for the CPSM in FIGS. 2C and 3B:

When the side panels are pulled laterally outwardly, also the points A', A", where the side panels are connected to the CPSM are pulled laterally outwardly, and the legs of the "Y" of the front and rear PM are hinged laterally outwardly, thusly foreshortening their effective longitudinal length, i.e. their length as projected onto the longitudinal center line 15. When combining this with the donning and the transformation from an essentially flat configuration into the generally U-shaped configuration (see FIG. 2B, C), this foreshortening lifts the pull means into the anal cleft of a user.

Concurrently with this lifting through the pull means, also the spreading means, and in particular the connecting regions 1303 and 1307 are lifted up along a line extending through the groin clefts rearwardly across the buttocks. This induces a cross-directional pull force along the SM strips 1312 and 1318, which further transmit these pull force to the discontinuity of the openings, which consequently open cross-directionally, thereby creating an even further foreshortening effect, albeit to a lesser degree than of the front and rear PM.

Thus, comparing FIGS. 3A and 3B, the longitudinal distance rear margin points A to front margin points F is significantly reduced in the in-use configuration, whilst the distance between points B and E is only slightly shorter.

This is a particular difference of the present invention to conventional approaches, see for example the above mentioned EP359410A1, wherein the elasticated secondary topsheet is spanning from one buttock to the other over the anal cleft, such that upon defecation faeces can migrate along the anal cleft and soil a large area of the skin. It should be noted that in the present invention this pull is a purely geometric effect, and does not require extensibility or elasticity of the employed materials. Within the present context, a material is considered non-elastic, if upon application of a strain corresponding to regular manufacturing conditions does not extend in its machine direction by more than 5%, preferably not more than 2% relative to its metered-in length.

Having thusly described the principle of the present invention, various not necessarily exclusive embodiments for the individual features are discussed further:

In FIG. 3A, the CPSM strip is depicted as a narrow strip, that may have a CD width just sufficient to accommodate the bonding and the separation lines, i.e. typically extending not less than about 5 mm cross-directionally from the longitudinal center line. From a functionality and material usage efficiency point of view, the strip does not need to be wider, though, e.g. for aesthetic reasons, it may extend laterally more towards, and mostly underneath, the overfolded portion, such that it would cover the full crotch width when the product is unfolded. As depicted schematically in FIG. 3D, the cross-directionally cut lines 1311, 1319 should extend sufficiently to allow free foreshortening of the topsheet material. Also the attachment at lateral edges of the wide CPSM strip is not of particular criticality except for not restraining the foreshortening, and is exemplarily shown (1490).

An alternative to implementing the spreading functionality is depicted in FIG. 4A, wherein SM strips 1312, 1318 are shown as partly separated strips from the overfolded portions 309 of the center piece 310, whereby the strips are partially separated, e.g., cut, therefrom and extend from and intersect a longitudinal overfolded side margin 314 of the center piece towards termination points 1322, 1328, which are positioned in the overfolded region but z-directionally overlapping the PM laterally outwardly of the discontinuity for the openings 304, 306, whereby the intersection of the longitudinally extending side margin is distanced less far away from the crotch point 305 than the termination points 1322, 1328 of the SM separation lines 1313, 1317. The SM strips are then connected to the PM in the proximity of the discontinuities for the openings 304, 306, respectively, then functioning essentially as described above.

Figure 4B:
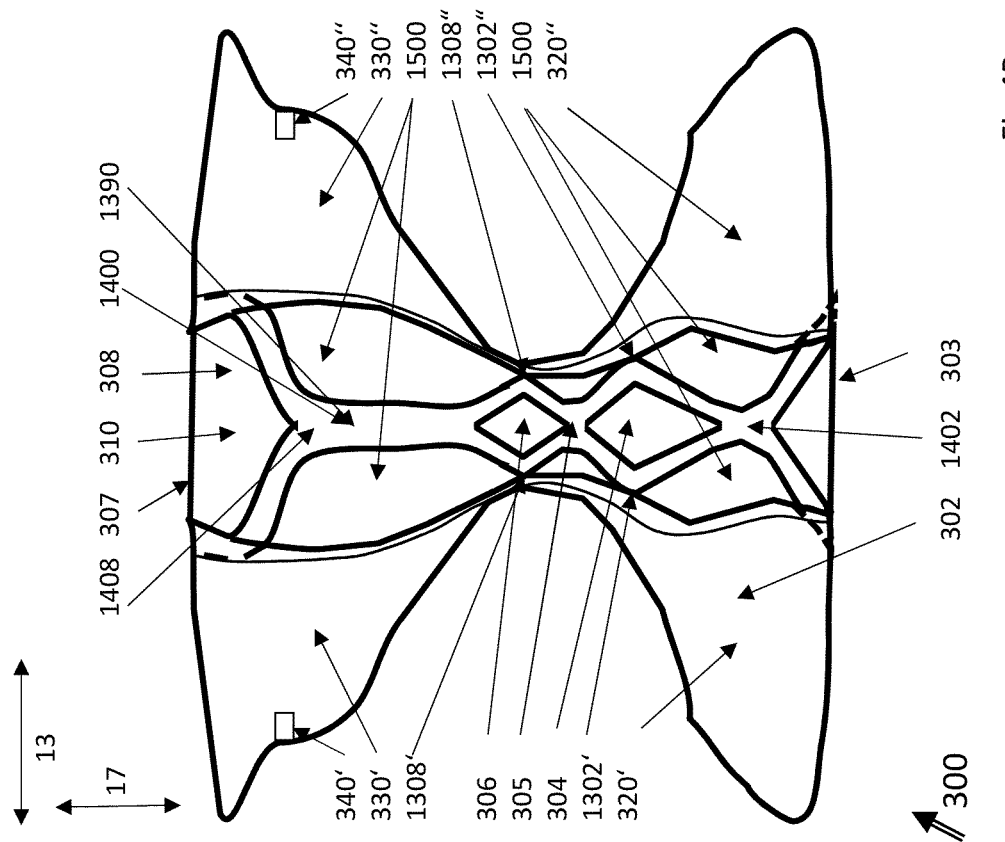
FIGS. 4 A and B and 5 A to H depict alternative executions of the element according to FIG. 3.

Referring to FIG. 4B, the overfolded portion may also be directly connected to the periphery of the opening, thereby directly inducing the spreading effect upon donning.

Further alternative embodiments relate to the execution of the pull means as a pull means strip 1410, see FIG. 5A to 5H. Whilst for the above explanation a CPSM was used that extends essentially over the full length of an article which comprises a front and a rear opening, see FIG. 5A, a number of applications only require a single opening, be this a rear one 306 in registry with the anus or a front one 304 in registry with genital organs. For all these embodiments, the front (1412) or rear margin (1418) of the PM strip 1410 coincides with the respective margins 303, 307 of the article.

Figure 5A:
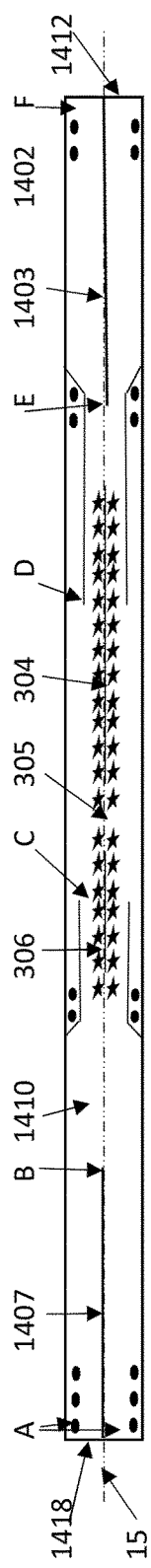
Figure 5C:
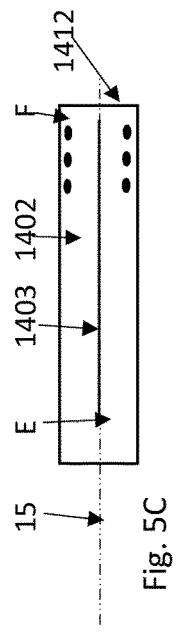
Figure 5E:
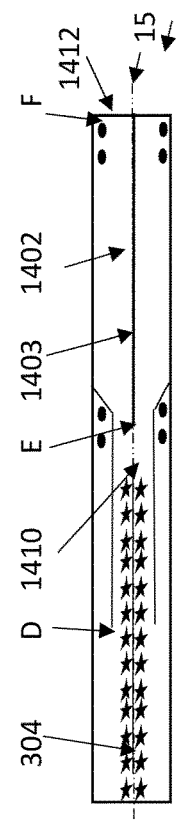
Figure 5B:
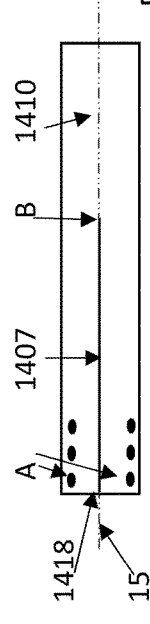
Figure 5D:
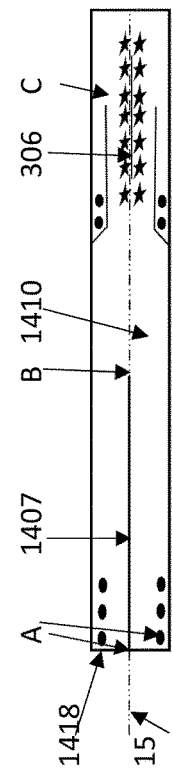

In the embodiment shown in FIG. 5B, the PM strip extends from the front margin 303 of the article towards the discontinuity for rear opening 306 but stops before reaching it. As shown in FIG. 5C, PM strip extends from the front margin 307 of the article towards the discontinuity for front opening 304 but stops before reaching it. Also for these embodiments, the overfolded portion is directly connected to the periphery of the opening, thereby inducing the spreading effect upon donning.

For the embodiment shown in FIG. 5E, the pull strip extends from the front margin 303 of the article towards and continues along the discontinuity for the front opening 304, also comprising a matching discontinuity, reaching into the crotch point region. Correspondingly, and shown in FIG. 5D, the pull strip may extend from the rear margin 307 of the article towards and continues along the discontinuity for the rear opening 306, also comprising a matching discontinuity, reaching into the crotch point region, or from the rear margin 307 of the article towards the discontinuity for front opening 304 but stops before reaching it (see FIG. 5F).

Figure 5G:
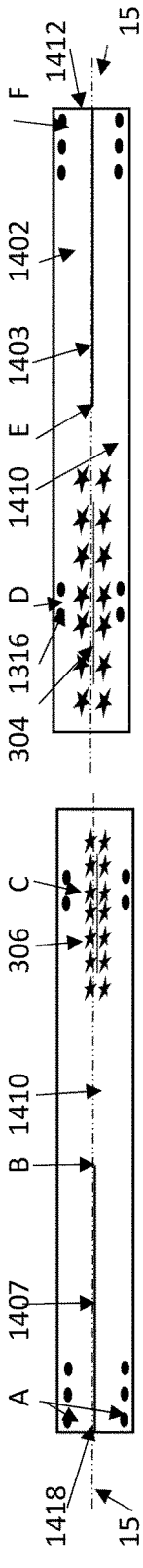
Figure 5F:
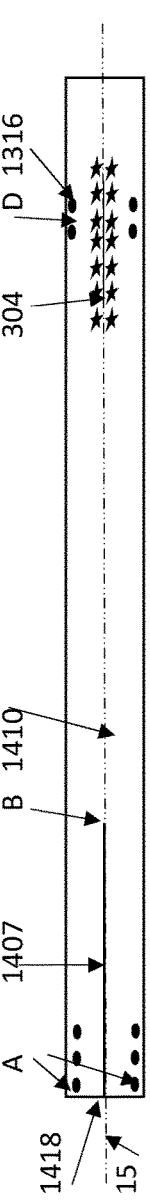
Figure 5H:
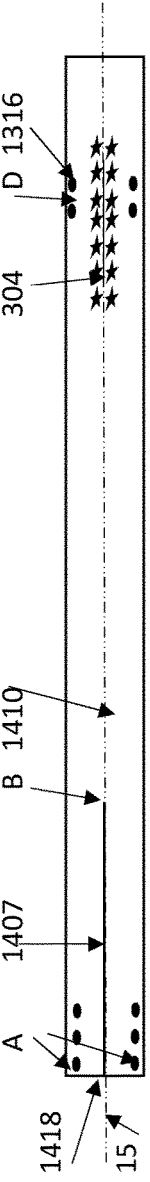

Even further embodiments may combine the options as shown in FIGS. 5G and 5H with the embodiments wherein SM strips (see 1312, 1318 in FIG. 4) are partly separated strips from the overfolded portions 309 of the center piece 310, resulting PM strip attachment points 1316 as shown in FIGS. 5G and H, respectively.

Further, the present invention encompasses various options for incorporating SPS 1500 and optional ESS 1600, adapted to the intended use and respective presence of openings, as further explained with reference to FIG. 6 A to G, depicting a cross-sectional view along the longitudinal center line 15, and FIG. 7 A to G depicting a top view onto the SPS with other features omitted.

In FIG. 7, the center piece is shown in a particular manufacturing configuration before overfolding of the longitudinal side margins 314 along fold lines 316 (as indicated representatively as dotted lines in FIG. 7A), i.e. also before being combined with a PM, SM, or CPSM. Optionally, and as indicated in FIGS. 6 and 7, the front and rear cross directional margins may be connected at that stage, as indicted by end margin connection 352, 358 at the front and rear margins, respectively. Further, an absorbent core 315, as may be applied to any other execution, is positioned between the backsheet 318 and the user oriented SPS 1500.

In order to be adapted to receive primarily faeces, the rear opening 306 is important. Whilst often not preferred, it might well be contemplated in this case to omit the absorbent core allowing to capture just faecal exudates. It may be well preferred that the SPS as uppermost layer is hydrophobic or even liquid impermeable so as to minimize any penetration of the liquids as contained in faeces back to the skin.

In case of primarily aiming at improved urine or menses handling the front opening 304 may be combined with a hydrophobic or liquid impermeable SPS, such that the urine or menses or the urine or menses releasing genital organs pass through the front opening 304 and the exudates may then be captured and preferably immobilized by an absorbent core.

In case of aiming at receiving faeces as well as urine and/or menses, there should be a rear opening 306 to allow faeces to pass though the SPS. It is further preferred that the SPS is hydrophobic or liquid impermeable in the rear portion of the article. As to the urine or menses receiving portion, both the application of hydrophilizer in the urine or menses receiving region as well as including a front opening may suitably be selected.

Further an exudate separation sheet (ESS) 1600 may suitably be introduced into the design. Such an ESS is positioned between an absorbent core and the SPS and connected to the latter in the crotch point region, extending rearwardly and or forwardly therefrom. The ESS may or may not allow liquids to pass through, or allow liquids to pass though only in one direction.

For most executions, it is preferred that the ESS is connected to the SPS in the crotch point region preferably by a firm, though soft and liquid impermeable connection that may preferably extend cross-directionally.

Whilst in the previous discussion, the less preferred option of a SPS with a front and a rear opening in the absence of an ESS has been described, FIG. 6A to G and 7A to G depict further options for the combination of this design variable.

In FIGS. 6A and 7A, the SPS 1500 comprises a single, rear discontinuity for the rear opening 306 and no ESS, as may be well suited for receiving faeces, and with a liquid permeable portion of the SPS in the regions of the genital organs for also allowing to receive urine.

FIGS. 6B and 7B are related to the addition of an ESS 1600, extending from the crotch point region rearwards and (in this view) underlying the SPS. As indicated, this creates a "pocket" essentially co-extensive with the SPS in the rear portion. The connection of the ESS to the SPS 1700 may be separate from or combined with other connections, e.g. the end margin connections 352, 358. This execution may preferably comprise a liquid permeable portion of the SPS in the regions of the genital organs for also allowing to receive urine.

FIGS. 6C and 7C relate to a similar execution as in FIGS. 6B and 7B, except that the ESS 1600 is not coextensive with the rear part of the SPS, but may be narrower or shorter, or—as depicted—both. As further depicted in FIG. 7C for the option of a rearwardly extending ESS and PM and no front opening, the ESS may comprise a cross-directionally extending separation line 1510, e.g. a cut line or a slit, just forward of the crotch point region, that will provide more comfort to a wearer by allowing the SPS to form a genital pocket where the SPS is not pulled towards the genitals.

FIGS. 6D and 7D depict yet a further execution as may be well suited to achieve a dry skin wherein the SPS may be executed as a hydrophobic or liquid impermeable web and yet fecal matter may be separated by an ESS extending into the front region. As shown, the ESS may be co-extensive with the SPS, though it may also be smaller, as indicated in FIGS. 6E and 7E.

The executions shown in FIGS. 6F and 7F comprise coextensive SPS and ESS over the full length, with a connecting line, preferably executed as a liquid barrier, in the crotch point region.

In yet a further execution, shown in 6G and 7G, the ESS extends over the full length, whilst the overlying SPS only covers the rear portion, both being connected in the crotch point region, preferably executed as a liquid barrier.

For the functionality of the present invention, it is not essential, if the PM is positioned z-directionally on top of (i.e. towards the wearer) or underneath (i.e. away from the wearer) the SPS. FIG. 8 A to C depict schematically and exemplarily a design with FIG. 8A showing a view onto the SPS 1500 prior to overfolding but already connected to the center piece (not visible) by connecting lines 1700, FIG. 8B after overfolding (indicated in FIG. 8A by folding arrows 1800) along folding lines 316, and FIG. 8C a cross-sectional view AA along the center line 15. The SPS 1500 extends over the full length and is separated, e.g. cut, along the center line 15 over the full length except for three non-separated sections 1522, 1525, and 1528, respectively. Further, a front (1532) and a rear (1538) cut out in the SPS, preferably as shown at a width of about the width of the PM strip 1410, is provided towards and reaching into the front (303) and rear margins (308), to allow proper bonding of the side margins to the thusly exposed PM after the overfolding. Further shown in FIG. 8A is a pull means strip 1410 underneath the SPS with its longitudinally extending side margins 1405 shown as dashed lines. Also the pull means strip 1410 is separated along the longitudinal center line 15 except for three non-separated sections 1422, 1425, and 1428 (see FIG. 8C). Further, ESS 1600 is positioned in the front portion underneath the SPS and PM, with at least its front margins coinciding with the ones of the SPS and its rear margin 1608 shown as dotted line in FIGS. 8A and B just rearwardly of the crotch point 305. The PM and the SPS are connected to each other in the front and rear (1712 and 1718, respectively) laterally outwardly of certain sections of the front (304) and rear (306) opening. The first surface of the SPS is connected to the overfolded portion to enable the spreading at front (1722) and rear (1728) SPS overfold connections. Further, the overfolded portion is connected to the PM strip through the front (1532) and rear (1538) cut out in the SPS at overfold-to-PM connections 1742 and 1748, respectively. Upon donning, the article will unfold as described in the above and shown in FIG. 2A, except that now the SPS is covering a major part of the PM strip, thereby giving a more pleasing appearance.

In order to avoid potential leakage in the areas of front and rear cut outs 5132, 1538, the ESS may extend from its crotch point margin 1608 forwardly towards and beyond the front margin of the SPS, and may during manufacturing extend into the rear margin of the preceding article. As illustrated in FIGS. 8D and E, this can be achieved by adding front masking connections 1912 to connect the ESS to the SPS along front masking connections 1912. Similarly, in the rear portion, a masking sheet 1900—as may be added separately but preferably is generated during manufacturing by extending the ESS as described above beyond the front margin of the SPS—may be added and connected to the SPS aside rear cut out 1538 by cut out connections 1918.

Figure 8F:
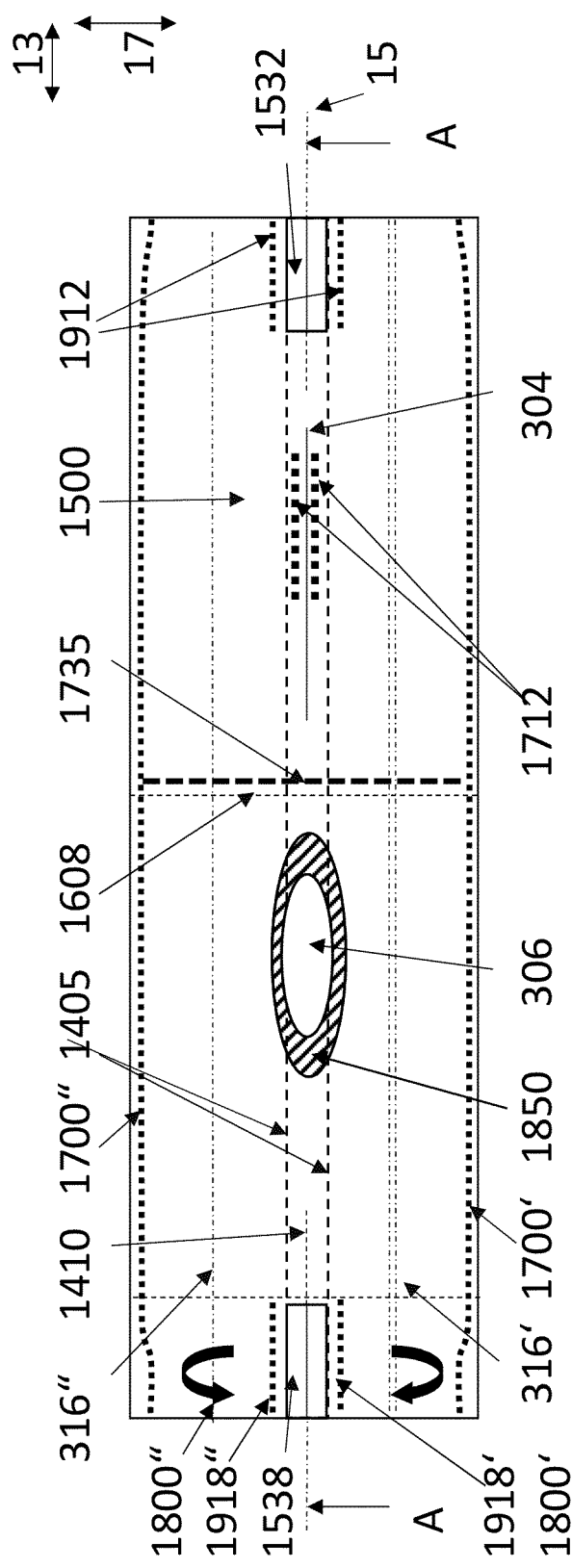
FIG. 8 A to H depict further particular exemplary executions of the present invention.

Yet a further execution of the present invention is depicted in FIG. 8F, relating to a different execution of the spreading means. In this execution, the opening, here explained for the rear opening 306, is not executed as a slit adapted to be cross-directionally pulled open, but the opening is executed as a cut out portion, here indicated by the oval shape. The cross-directional opening is maintained during use by a reinforcement means, here shown as a peripheral reinforcement 1850. Such a reinforcement may be a soft ring as cut as a thin slice with a thickness of less than 3 mm, preferably less than 2 mm or even less than 1 mm from a hollow cylinder of a soft material, such as—without limitation— silicone or rubber. The ring slice may be applied to the PM by a rotary applicator or other suitable means and be connected by suitable adhesive (not shown). The reinforcement means may also be shaped in situ, such as by applying a material in a fluid or softened state, e.g. by conventional printing apparatus. Such a material may be a conventional hot melt adhesive, with sufficient softness in a cold state. It may also be a skin adhesive, such as described in WO2000/000235A1.

A further execution of the present invention is depicted in FIGS. 8G and 8H. In FIG. 8G an article is depicted in analogy to the one as shown in FIG. 8D. However, a front (2002) and a rear (2008) cut out is applied to the backsheet 318 (se FIG. 8 H) and front (2012) and rear (2018) cut connections are applied to connect the backsheet laterally outwardly of the cut out to the SPS 1500. A PM strip 1410, as can be positioned z-directionally between the absorbent core 315 and the SPS 1500 in the crotch region of the article, as described in the above, is extending at least through the backsheet cut out 2008 but most preferably also though the front backsheet cut out 2002. If present, the ESS 1600 and the absorbent core 315 stop short of this cut out, see front ESS margin 1602, with the front and rear core margins not shown in FIG. 8G. The front and rear ends of the PM strip 1410 comprise a PM strip fixation means 2022 and 2028, respectively, as may very suitably be executed as a mechanical fastener hook patch, as well known in the art. Such a patch may be applied with its engaging surface towards the SPS, as exemplarily shown in FIG. 8H in the front region with fixation means 2022 and fixation means engaging surface 2023. Such a patch may also be applied with its engaging surface towards the side panels (not shown), as exemplarily shown in FIG. 8H in the rear region with fixation means 2028 and fixation means engaging surface 2027. In contrast to the executions as described hereinabove, such a design allows to activate the MD foreshortening after the article is donned to the user, such that the degree of foreshortening—and hence the pull into the anal cleft—can be adjusted according to the specifics of the user. To this end, the article is donned and thereafter the PM strip is pulled and affixed on the article laterally outwardly by the PM strip fixation means. For such a design, the PM strip may also be executed as an elastic strip, which may then be stretched so as to at least partially encircle the waist of the wearer, thusly aiding the waist fixation on the body.

The skilled person will also appreciate that any further exudate handling means, such as liquid or faeces acquisition features, may be incorporated into or added to the absorbent core or be positioned between the absorbent core and the SPS or ESS.

All discontinuities may also be executed as partly separated lines, where the separation is incomplete, such as by an intermittent cutting line or a perforation line (sometimes also referred to as "perf 'n pop"), such that the material remains connected during at least a part of the process, but is readily separated at least upon donning and in the in-use configuration. For the front and rear openings the x-y-extension will be formed from the respective separation lines upon the transition from the manufacturing configuration into the in-use configuration. Whilst the discontinuity may be and often preferably is executed as a separation line, such as a cut, it may also be formed by removing material from the web so as to form an opening already at this point in the manufacturing configuration. The connecting of the various elements may be achieved by any conventional means, such as without limitation heat or pressure bonding, or sonic, preferably ultrasonic bonding, though especially for the connections involving the overfolded regions, use of appropriate glues is preferred from a processability point of view.

As a skilled person will readily realize, the term "point", e.g. "connecting point", may exhibit a certain size, e.g. corresponding to the applied technology for connecting. Thus a glue-type connecting point includes a patch of glue sufficiently small to not impact functionality in the surrounding region. Similarly, the term "line", e.g. "connecting line" may exhibit a certain width. Also the term encompasses an interrupted line, e.g. comprising a dotted glue or ultrasonic bonding line, as well as a bonding pattern, such as a line made of a multiplicity of (sub-) lines or a connecting point made of a multiplicity of smaller bond points. Similarly, the term "region" encompasses a long but narrow region that may also be seen as a "line".

The width of the CPSM has to be at least the overfolding gap width as the distance of the overfolded side margins to each other, plus the machining tolerance for positioning and connecting the CPSM to the overfolded regions. This machining tolerance may be very small, e.g. less than about 5 mm, but should not exceed about 10 mm or 20 mm for material usage efficiency reasons. Generally, the SPS, PM, CPSM, or SM can be made from a broad range of raw materials satisfying the general requirements that apply to hygiene articles to be worn on the lower torso of a wearer, such as not compromising on comfort or health aspects. Routine adaptation to the specific application will determine strength, softness, air- and liquid permeability, etc., of the materials. Particularly when the articles are intended for large scale production, the materials are preferably web materials.

Generally, the term "web" relates to any material which is essentially endless or continuous in one direction (generally denoted as "x-direction" or "machine direction"). Webs are often, but not necessarily, stored, supplied or used in roll form and thusly also sometimes denoted "roll goods". Whilst these are then not "endless" in the strict sense of the word, their extension in this x-direction is significantly larger than in any other direction. By combining consecutive rolls or other batches, ("splicing") such webs can be considered "endless" for all practical purposes. Webs may be transported in a "batch" form, such as when a roll thereof is shipped, or they may follow a "web path", such as when the webs are unwound from a roll, as described hereinafter. Typical examples for webs are—without implying any limitation—plastic films or foils, optionally apertured, textiles, non-wovens, nets, or scrims.

The SPS and the pull strip materials are preferably compliant, soft feeling, and non-irritating to the wearer's skin and may be manufactured from a wide range of materials, such as porous foams; reticulated foams; apertured plastic films; or woven or nonwoven webs of natural fibres (e.g. wood or cotton fibres), synthetic fibres (e.g. polyester or polypropylene fibres), or a combination of natural and synthetic fibres. If they include fibres, the fibres may be spunbonded, carded, wet-laid, meltblown, hydroentangled, or otherwise processed as is known in the art. They may be a composite material, such as when comprising an open net or scrim structure in combination with a spunbonded web.

Preferably, the SPS exhibits a low tendency for the passage of faeces. Optionally, the SPS may exhibit a z- or thickness directional gradient structure, or be a laminate or composite material, such as exhibiting particularly skin friendly properties on the user oriented surface, or particular faeces absorbent properties on the opposite surface, which may be particularly beneficial in the context of low viscosity or "runny" faeces.

Optionally, the SPS may be a composite material, such as being made in stripes (y-directional variation) or connected patches (x-directional variation).

Optionally, the SPS may comprise additives, such as skin friendliness enhancer, such as emollients or the like, as well known in the art.

For executions where the SPS extends more forwardly into regions of urine or menses loading without a front opening, it should exhibit—at least in these regions—good liquid permeability, such as by being hydrophilic by nature of the materials employed or by treatment. For executions comprising a front opening allowing exudates to pass through, it may be preferred that the SPS is fluid impermeable, e.g. as a hydrophobic nonwoven, a film, or a composite thereof.

For any execution of the present invention, the longitudinal extensions of the various regions of the SPS, PM, or CPSM preferably do not vary significantly in their relative length independent of the overall length and in particular also independent of the length of the combined article on a wearer, i.e. if designed for an adult or a baby. In order to better describe the relative dimensions, the distance of the rear waist margin of the SPS to the front waist margin is set to 100%, and then the following ranges are preferred for the following distances between characteristic point in a manufacturing configuration, wherein the precursor of the article corresponds to the overall length of the article:

| | |
|---|---|
| from the rear waist margin A to "node" point B: | 10% to 25%; |
| from connection B to C: | 20% to 40%; |
| from C to D: | 15% to 25%; |
| from D to E: | 5% to 25%; |
| from E to F: | 10% to 25%, | whereby the respective percentage figures should add up to 100% and—if a characteristic point, e.g. of a further opening, is not present, the neighbouring ranges for this notional point are combined.

It should be noted, that the length forwardly of the anal discontinuity is not of great relevance for ensuring the functionality of the executions of the present invention.

Figure 9:
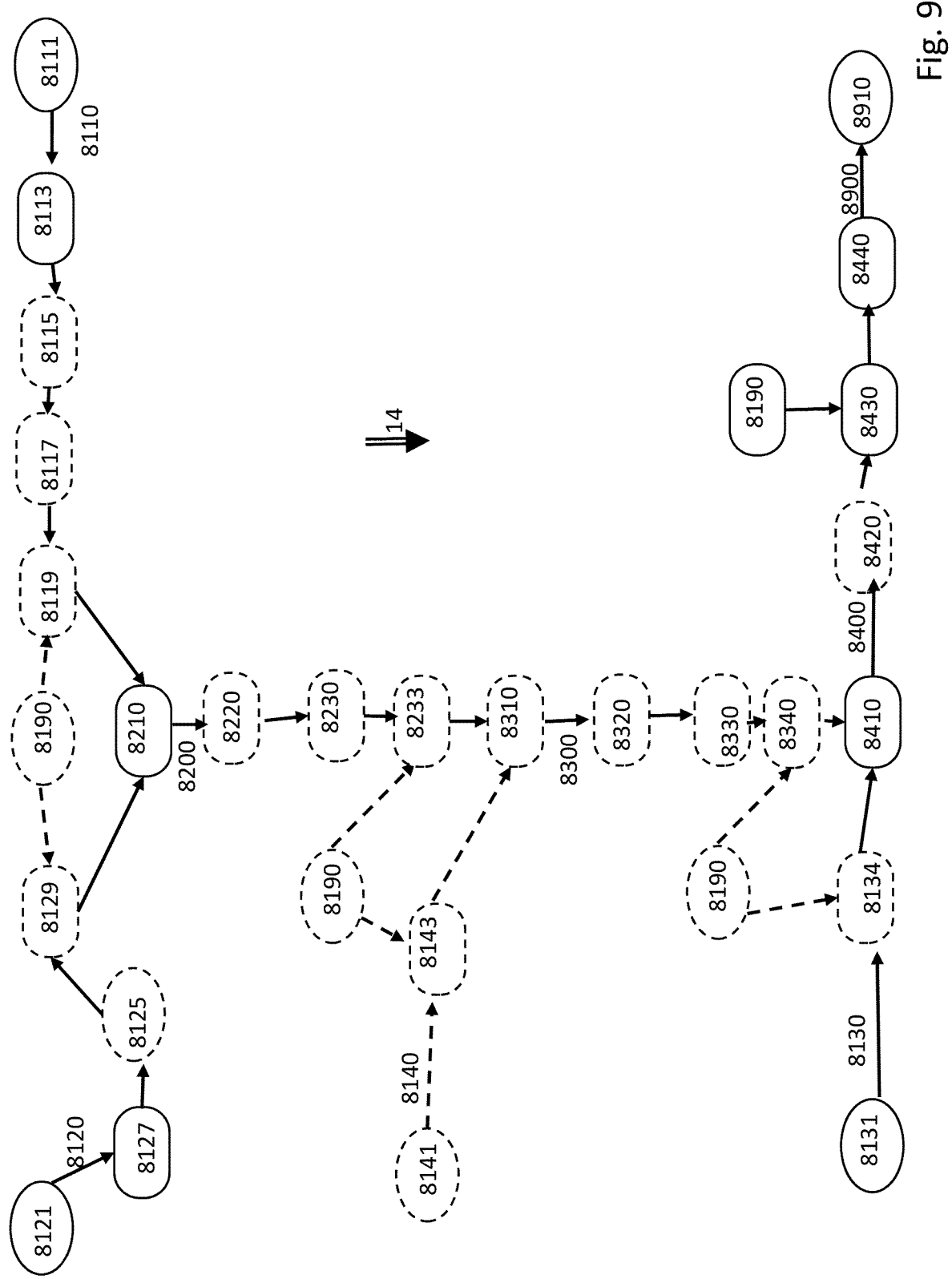
FIG. 9 depicts a flow chart for a process for making hygiene articles according to the present invention.

In another aspect, the present invention relates to the manufacturing of such hygiene articles, as described in the context of FIG. 9.

Generally, the process can be executed on equipment comprising units as well known in the art for the manufacturing of hygiene articles, and is typically a continuous process of combining, handling and treating essentially continuous web materials, optionally upon addition of other materials like adhesives or powders, until at the end of this continuous process the hygiene article is separated from the precursor composite web, followed by further processing, like further folding and packaging. Accordingly, the equipment for executing the present invention requires at least unwind stands for the various web materials;

web guide means so as to control positioning and tensioning of the web materials;

separation means, such as rotating knives, for severing pieces from the web materials, and for applying essentially machine directionally separation lines, such as slits;

combining means for placing webs or pieces of webs in a predetermined relative positioning, optionally in combination with separation means, such as so called "cut and place" units;

folding means for applying longitudinal folds along predetermined longitudinal fold lines, and optionally also cross-directional folds at least at the final stage of the product making;

connecting means, including a adhesive bonding, typically though not necessarily of the hot-melt glue type, with application of glues onto a predetermined glue region, as may be a dot, a line, or an area, combining the materials in the predetermined relative positioning;

making the connection permanent under normal in-use conditions such as by curing, hardening, or most preferred by cooling;

melt fusion boding, such as by applying heat and/or pressure, friction, or preferably sonic, more preferably ultrasonic energy, to a bonding point, line or area;

All of these equipment units as well as usual drive and control means for operating a manufacturing line are well known to a person skilled in the art of hygiene article manufacturing.

According to the present invention, the multiple product variants imply multiple process options, as will be explained by referring to FIG. 9. As indicated in FIG. 9, the process runs along a general process direction 14 that is aligned with the longitudinal orientation of the finished article. It should be noted that the explanation is not necessarily following the time line of the process, i.e. process steps as explained later may be executed concurrently or even earlier than other process steps. Steps that are essential for executing the present invention are indicated with solid lines, optional steps or material flow lines with dashed lines.

Thus the process comprises the steps of providing the raw materials:

Providing a center piece web 8130 by supplying it (8131) by a center piece supply unit as may be an unwind stand or a box, or this web may be formed in upstream process steps from individual web materials, comprising a backsheet, side panels and optionally an absorbent core. The CP comprises repeating lengths that correspond to the overall length of the finished hygiene article, thereby exhibiting a front and rear cross-directional end-margin, be this recognizable in the continuous web, such as by a marker, or by the process settings.

Providing a SPS web material 8120 that may be executed as the topsheet material of the center piece or by suppling it (8121) by SPS supply means.

Providing a pull means web material 8110 by supplying it (8111) by PM supply means.

Optionally providing an ESS web material 8140 by supplying it (8141) by ESS supply means.

Providing adhesives or glues 8190 to apply the glue by glue applicators at various optional or essential process steps.

Optionally providing reinforcement material (RM) from a RM supply means.

As has been described in the above, the spreading means can be provided by several options, namely
- by providing spreading means strips as may be partially separated
  - from the CPSM material) or
  - from the longitudinally overfolded portions of the center piece;
- by connecting the longitudinally overfolded portions of the center piece to the user oriented surface of the SPS adjacently to the separation line for forming the opening.

Longitudinal separation lines are applied (8113) to the pull means web material 8110 as waist separation lines along the longitudinal center line before the pulls means are combined with the SPS, such that these extend after combination with the center pieces away from the front or rear margin, but not over the full length of the pull means. Optionally, for the option that the PM and the SM are unitary (combined Pull and Spreading Means), partial separation lines may be applied (8115). If the PM is intended to reach into the anal and or genital region and respective openings, corresponding separation lines may be applied (8117). These steps may be executed separately or in a single processing unit.

At least one longitudinal separation line corresponding to the rear and/or front opening has to be applied (8127) to the SPS, regardless if this is provided as separate material 8120 or if this is already combined with the pull means. Further, for options with the PM positioned under the SPS, at least a cutout aside the product center line in one of the waist regions have to be provided in the SPS (8125), at a length corresponding to the length and position of the overfold to PM connection, and at a width corresponding to the width of the PM before the SPS is combined to the backsheet.

Optionally, especially for options wherein the SPS is already combined with the center piece, glue as provided from glue supply 8190 may be applied to the SPS (8119) and/or the PM (8129) at the periphery of the separation lines that correspond to the rear or front opening.

If a reinforcement means combined with a cutout is used to form the at least rear opening, the combing of the reinforcement means with the SPS and the subsequent cutout are executed prior to combining the combined SPS/reinforcement means web with the PM.

The combining 8210 of the PM 8110 and the SPS (8210) to form the SPS-PM composite 8200 may be achieved by separating pieces of the PM and positioning these, e.g. by cut and space units, on the SPS web 8120. If pieces of SPS 8120 are to be combined with a full length PM 8110, or another full length web, the infeed into the cut & place unit should be switched accordingly. In case of a glue connection (8119/8129), the bond may be strengthened by a roller, optionally a chilled roll. Alternatively, and preferred if the SPS is not yet combined with the center piece, applying the glue to the SPS or PM is omitted, and the connecting is achieved by melt-fusion bonding 8220, preferably ultrasonic bonding. If the separation lines for the openings are already applied to the SPS (8127) and PM (8117) prior to the combining 8210, this must be achieved with utmost precision. Hence it may be preferred that these separation lines are applied to both the SPS and the PM simultaneously (8230) after the combination.

If an ESS 8140 is to be included as supplied 8141 from an ESS supply unit, it may be suitably combined 8310 with the PM-SPS composite 8200 to form the PM-SPS-ESS composite 8300 by conventional units, such as cut and place units, if it is shorter than the SPS. Preferably, the connecting of the ESS and the PM-SPS composite, including the connection along the front and rear SPS cutouts, if present, is by melt-fusion bonding 8320, more preferably by ultrasonic bonding, though it can also be achieved by applying glue 8190 to the ESS 8143 and/or to the PM-SPS composite 8233. Options wherein the ESS extends over the full article length and the SPS is covering only a portion (see e.g. FIGS. 6G and 7G) are executed mutates mutandis. Similarly, the masking sheet may be applied during the manufacturing process as an extension of the front ESS beyond the article margin into the rear portion of an adjacent article, such that no additional supply means for this sheet becomes necessary. The PM-SPS-ESS composite 8300 can now be combined 8410 with the center piece 8130 to form a flat article precursor 8400, by cutting the PM-SPS-ESS composite 8300 to length, if needed. The connecting between this composite 8300 and the centerpiece 8130 is preferably by melt-fusion bonding 8420, more preferably by ultrasonic bonding, though it can also be achieved by glue applications 8134 and 8340, respectively, to the composite 8300 and/or to the centerpiece 8130 with glue supplied from glue supply 8190.

In an optional design execution, wherein the SM is executed as partially cut separation strips from the overfolded portion, the separation lines to form the strips may be applied 8420 prior to performing the overfolding.

Prior to or simultaneously with overfolding 8440, glue as provided from a glue supply 8190 is applied 8430 to the flat article precursor 8400 at the respective connecting points of the PM, SM, CPSM, or center piece as described in the above.

The overfolding 8440 is executed by conventional means, such as guide rails or fingers. Optionally, the fold can be stabilized by a set of pressure rolls (not shown).

Thus, an essentially continuous web with a sequence of overfolded hygiene article precursors 8900 can now be delivered to final processing steps 8910, where it may be cut into the sequence of individual articles, undergo further folding and packaging.

The skilled person will also readily realize, that the process may comprise further processing steps, such as application of closure means, closing of side panels to form pants style articles, application of wetness indicators, etc.

The invention claimed is:

1. A hygiene article for wearing on the lower torso of a wearer and adapted to receive and retain bodily exudates, said article exhibiting a length/longitudinal/x-direction, a width/cross-directional/y-direction, perpendicular to the length/longitudinal/x-direction and corresponding to a left-right orientation of a user during use, a thickness/z-direction, perpendicular to both, and a longitudinally extending center line, said article comprising, relative to a wearer during use, a rear waist region and a front waist region, each comprising cross-directionally opposite first and second side panel sections and a center section there between, and a crotch point region positioned longitudinally between said waist regions, and a crotch point positioned between an anal opening and genital organs of a wearer during use, said article being adapted to be converted from a manufacturing configuration, into an in-use configuration, wherein said hygiene article adopts a general U-shape by said longitudinally extending center line extending from the front or rear waist region of a wearer through the crotch point region into the opposite waist region of the wearer, and wherein said front and rear waist regions are adapted to encircle a waist of a wearer, said article further comprising:
a skin protection sheet (SPS) comprising an upper SPS surface intended to be in direct contact with the skin of a wearer at least in portions of at least one of said front and rear waist portions; and an opposite SPS surface;
said SPS further comprising at least one opening adapted to be in an in-use configuration in registry with a bodily exudate releasing body opening or a genital organ; and
said SPS extending from said front or said rear waist regions at least into the crotch point region of said article;
said article further comprising:
an essentially non-elastic longitudinal foreshortening pull means (PM);
at least a cross-directional spreading means (SM);
a backsheet adapted to retain bodily exudates in said article positioned opposite of said outer surface of said SPS;
side panels extending laterally outwardly of said SPS at least in an in-use configuration
said article being characterized in that
in said manufacturing configuration
said SPS comprises longitudinal side margins that are overfolded along a longitudinal fold line towards but not over said longitudinal center line of said article,
said pull means being positioned essentially along said longitudinally extending center line, and against the upper or opposite surface of the SPS; and said pull means extending from at least one of said longitudinal side margins in the front or rear waist region of said SPS towards said crotch point, and if covering said opening(s) of said SPS, said pull means further comprises (a) pull means opening(s) in registry with said openings(s) of said SPS;
said pull means being connected in the front or rear waist regions to overfolded portions of said SPS;
said pull means comprising a longitudinally extending waist separation line aligned with the longitudinally extending center line of the article, extending from said front and/or rear waist regions towards but not into said at least one opening of said SPS, and allowing to pull front or rear ends of said pull means laterally outward to foreshorten the available longitudinal extension;
said pull means further, in case of extending into an opening, comprising a pull means opening in registry with said SPS opening(s);
said spreading means (SM) being selected from the group consisting of (1) a connection of said overfolded portions of said SPS to the outer surface of said SPS or PM laterally outwardly of said opening; (2) a pull means strip partially cut from said pull means by a separation line extending from and intersecting a longitudinal side margin of said pull means towards but terminating at a termination point before intersecting said pull-means opening, wherein said intersection of said longitudinally extending side margin is distanced further away from said crotch point than the termination point of said separation line, said pull means strip being connected at a laterally outward end of said pull means strip to said overfolded portions of said SPS; (3) an overfold strip, partially cut from said overfolded portion of said SPS by a separation line extending from and intersecting a longitudinal overfolded side margin of said SPS towards a termination point laterally outwardly of said opening, wherein said intersection of said longitudinally extending side margin is distanced less far away from said crotch point than said termination point; and (4) a reinforcement means adapted to maintain a pre-cut opening cross-directionally open, wherein in said in-use configuration, said SPS is adapted to be lifted z-directionally to fit into an anal cleft of a wearer by said PM, and said at least one opening of said SPS is maintained cross-directionally open by said SM.

2. The hygiene article according to claim 1, wherein for said overfold strip, when partially cut from said overfolded portion of said SPS by a separation line, said termination point is positioned such that said termination point z-directionally overlays said PM or said SPS.

3. The hygiene article according to claim 1, wherein in a manufacturing configuration, said PM exhibits a cross-directional extension that is larger than a cross-directional distance of overfolded longitudinal extending side margins of a center piece, wherein the SPS is connected to a proximity of at least one discontinuity.

4. The hygiene article according to claim 1, wherein at least said SPS and SM are essentially non-elastic.

5. The hygiene article according to claim 1, wherein in a manufacturing configuration a precursor of the article exhibits an overall article length, and wherein the precursor comprises sections that are separated by characteristic points along the longitudinal center line, wherein distances between the characteristic points exhibit the following ranges:
from a rear waist margin to a forward end of the waist separation line: 10% to 25%;
from the forward end of the separation line to a midpoint point of a rear discontinuity: 20% to 40%;
from the midpoint of the rear discontinuity to a midpoint point of a front discontinuity: 15% to 25%;
from the midpoint point of the front discontinuity to a rearward end of a front waist separation line to the front: 5% to 25%;
from the rearward end of the front waist separation line to a front waist margin: 10% to 25%, wherein the respective percentage figures should add up to 100% corresponding to the overall article length and wherein, when certain features are not present, the distances are counted to the next characteristic point.

6. The hygiene article according to claim 1, wherein said article is an absorbent article, selected from the group consisting of baby diapers, adult incontinence article and feminine hygiene article.

7. The hygiene article according to claim 1, further comprising an absorbent core positioned z-directionally between said SPS and said backsheet.

8. A hygiene article for wearing on the lower torso of a wearer and adapted to receive and retain bodily exudates, said article exhibiting a length/longitudinal/x-direction, a width/cross-directional/y-direction, perpendicular to the length/longitudinal/x-direction and corresponding to a left-right orientation of a user during use, a thickness/z-direction, perpendicular to both, and a longitudinally extending center line,
- said article comprising, relative to a wearer during use, a rear waist region and a front waist region, each comprising cross-directionally opposite first and second side panel sections and a center section there between, and a crotch point region positioned longitudinally between said waist regions, and a crotch point positioned between an anal opening and genital organs of a wearer during use,
- said article being adapted to be converted from a manufacturing configuration, into an in-use configuration, wherein said hygiene article adopts a general U-shape by said longitudinally extending center line extending from the front or rear waist region of a wearer through the crotch point region into the opposite waist region of the wearer, and wherein said front and rear waist regions are adapted to encircle a waist of a wearer,
- said article further comprising:
  - a skin protection sheet (SPS) comprising an upper SPS surface intended to be in direct contact with skin of a wearer at least in portions of at least one of said front and rear waist portions; and an opposite SPS surface;
  - said SPS further comprising at least one opening adapted to be in an in-use configuration in registry with a bodily exudate releasing body opening or a genital organ; and
  - said SPS extending from said front or said rear waist regions at least into the crotch point region of said article;
- said article further comprising:
an Exudate Separation Sheet (ESS)
positioned adjacent to said opposite SPS surface,
being connected to said SPS at least in the crotch point region;
and extending from said crotch point region towards at least one of the front and rear waist regions,
  an essentially non-elastic longitudinal foreshortening pull means (PM);
  at least a cross-directional spreading means (SM);
  a backsheet adapted to retain bodily exudates in said article positioned opposite of said outer surface of said SPS;
  side panels extending laterally outwardly of said SPS at least in an in-use configuration
said article being characterized in that
  in said manufacturing configuration
  said ESS comprises longitudinal side margins that are overfolded along a longitudinal fold line towards but not over said longitudinal center line of said article,
  said pull means being positioned essentially along said longitudinally extending center line, and against the upper or opposite surface of the SPS; and said pull means extending from at least one of said longitudinal side margins in the front or rear waist region of said ESS towards said crotch point, and if covering said opening(s) of said SPS, said pull means further comprises (a) pull means opening(s) in registry with said openings(s) of said SPS;
  said pull means being connected in the front or rear waist regions to overfolded portions of said ESS;
  said pull means comprising a longitudinally extending waist separation line aligned with the longitudinally extending center line of the article, extending from said front and/or rear waist regions towards but not into said at least one opening of said SPS, and allowing to pull front or rear ends of said pull means laterally outward to foreshorten the available longitudinal extension;
  said pull means further, in case of extending into an opening, comprising a pull means opening in registry with said SPS opening(s);
  said spreading means (SM) being selected from the group consisting of (1) a connection of said overfolded portions of said ESS to the outer surface of said SPS or PM laterally outwardly of said opening; (2) a pull means strip partially cut from said pull means by a separation line extending from and intersecting a longitudinal side margin of said pull means towards but terminating at a termination point before intersecting said pull-means opening, wherein said intersection of said longitudinally extending side margin is distanced further away from said crotch point than the termination point of said separation line, said pull means strip being connected at a laterally outward end of said pull means strip to said overfolded portions of said ESS; (3) an overfold strip, partially cut from said overfolded portion of ESS by a separation line extending from and intersecting a longitudinal overfolded side margin of said ESS towards a termination point laterally outwardly of said opening, wherein said intersection of said longitudinally extending side margin is distanced less far away from said crotch point than said termination point; and (4) a reinforcement means adapted to maintain a pre-cut opening cross-directionally open,
wherein in said in-use configuration, said SPS is adapted to be lifted z-directionally to fit into an anal cleft of a wearer by said PM, and said at least one opening of said SPS is maintained cross-directionally open by said SM.

9. The hygiene article according to claim 8, wherein said ESS is selected from the group consisting of hydrophilized nonwoven material, hydrophobic nonwovens, films, apertured films, and combinations thereof.

* * * * *